United States Patent [19]

Kasha et al.

[11] Patent Number: 4,689,345

[45] Date of Patent: Aug. 25, 1987

[54] OXYGENATED ALKYL SUBSTITUTED BICYCLO ALKANES

[75] Inventors: Walter J. Kasha, Los Angeles; Chantal S. Burnison, Beverly Hills, both of Calif.

[73] Assignee: CBD Corporation, Los Angeles, Calif.

[21] Appl. No.: 838,760

[22] Filed: Mar. 12, 1986

Related U.S. Application Data

[63] Continuation-in-part of Ser. No. 795,527, Nov. 6, 1985, abandoned, which is a continuation-in-part of Ser. No. 567,172, Dec. 30, 1983, abandoned, which is a continuation-in-part of Ser. No. 550,290, Nov. 8, 1983, abandoned, which is a continuation-in-part of Ser. No. 375,755, May 6, 1982, abandoned, and Ser. No. 560,310, Oct. 28, 1983, abandoned, which is a continuation-in-part of Ser. No. 492,060, May 6, 1983, abandoned, and Ser. No. 546,299, Oct. 28, 1983, abandoned, which is a continuation-in-part of Ser. No. 492,059, May 6, 1983, abandoned, and Ser. No. 549,306, Oct. 28, 1983, abandoned, which is a continuation-in-part of Ser. No. 492,058, May 6, 1983, abandoned.

[51] Int. Cl.[4] .................. A61K 31/12; A61K 31/22
[52] U.S. Cl. ...................... 514/546; 514/691; 514/729
[58] Field of Search ............. 514/691, 546, 715, 729

[56] References Cited

U.S. PATENT DOCUMENTS 4,000,174  12/1976  Henrick et al. ............... 260/455 R
4,292,432  9/1981   Ono et al. ..................... 549/35
4,322,435  3/1982   Kojima et al. ................. 424/305

FOREIGN PATENT DOCUMENTS 65329    11/1975  Australia .
2193612  2/1974   France .
2419271  10/1979  France .
2040928  9/1980   United Kingdom .

OTHER PUBLICATIONS

Ford et al., "Anti-Neoplastic Effects of Metcyclor".
Ford et al., "Modulation of Connective Tissue Metabolism by Steroid Hormones and Ethocyn".
King et al., "Effects of Cyoctol vs. 13-Cis Retinoic Acid on Dihydrotestosterone Receptor Binding in Human Facial Sebacious Glands".
Ford et al., "Dense Intraabdominal Adhesions–A Manifestation of Localized, Hyper-Androgen Receptors".
Ford et al., "Differential Androgen Receptor Activity in Patients with Androgenic alopecia and the Effects of Cyoctol on Dihydrotestosterone (DHT) Protein Binding".
King et al., "Effects of Cyoctol vs. 13-Cis Retinoic Acid on Dihydrotetosterone (DHT) Receptor Binding in Human Facial Skin Fibroblasts".
Hammill et al., "Effects of Cyoctol on the Hormonally Stimulated Increases in DNA and RNA Metabolism in Fungi".
Hammill et al., "Dihydrotestosterone and Estradiol Receptors in Trichomonas Vaginalis and the Effects of Cyoctol".
King et al., "Increased Androgen Binding in Keloids and its Inhibition with Cyoctol".
Selim et al., "Absorption, Tissue Distribution, Blood Level and Excretion of [14]C Labeled Cyoctol Following Oral or Dermal Administration", Abstract presented at 6th CIRD Symposium, Cannes, France, Oct. 1985.

Primary Examiner—Leonard Schenkman
Attorney, Agent, or Firm—Wegner & Bretschneider

[57] ABSTRACT

Anti-androgenic composition compound of the formula

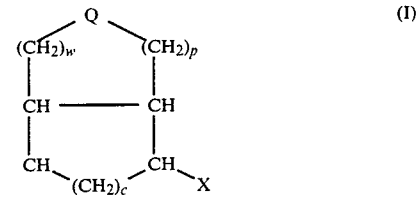

wherein
Q is CO, CH(OR), CR(OH), or CR (OC)-lower alkyl);
R is H, or $C^{1-2}$-alkyl;
X is hydroxyalkyl, methoxy-$C^{2-11}$-alkyl, ethoxy-$C^{2-11}$-alkyl or oxo-$C^{2-11}$-alkyl, formyl-$C^{2-11}$-alkyl, carboxy-$C^{2-11}$-alkyl or ($C_{1-2}$-alkyl) oxycarbonyl-$C^{2-11}$-alkyl;
c is 1 or 2;
p or w are 0, 1 or 2 and the sum of p and w is 1 to 4;
and a pharmaceutically acceptable salt thereof.

19 Claims, No Drawings

OXYGENATED ALKYL SUBSTITUTED BICYCLO ALKANES

This is a continuation-in-part of application Ser. No. 795,527, filed Nov. 6, 1985 now abandoned, which in turn is a continuation-in-part of Ser. No. 567,172, filed Dec. 30, 1983 now abandoned, which in turn is a continuation-in-part of Ser. No. 550,290, filed Nov. 8, 1983 now abandoned, which in turn is a continuation-in-part of Ser. No. 375,755, filed May 6, 1982 now abandoned, and Ser. No. 560,310, filed Oct. 28, 1983 now abandoned, which in turn is a continuation-in-part of Ser. No. 492,060, filed May 6, 1983 now abandoned, and Ser. No. 546,299, filed Oct. 28, 1983 now abandoned, which in turn is a continuation-in-part of Ser. No. 492,059, filed May 6, 1983 now abandoned, and Ser. No. 549,306, filed Oct. 28, 1983 now abandoned which in turn is a continuation-in-part of Ser. No. 492,058, filed May 6, 1983 now abandoned.

The present invention provides compounds of the formula:

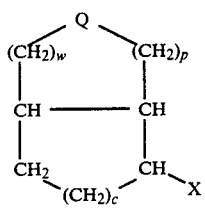
(I)

wherein

Q is CO, CH(OR), CR(OH) or CR(OCO-lower alkyl) R is H or $C^{1-2}$-alkyl;

X is hydroxyalkyl, methoxyalkyl, ethoxyalkyl, $C_{1-2}$-alkylcarbonyloxy-$C^{2-11}$-alkyl, oxoalkyl, formylalkyl, or carboxyalkyl in which the main alkyl moiety contains 2-11 carbon atoms;

c is one or two;

p and w are zero or one or two and the sum of p and w is one to four;

and a pharmaceutically acceptable salt thereof.

As the pharmaceutically acceptable salts may be mentioned, for example, alkali metal salts, alkaline earth salts and ammonium salts. As specific salts may be mentioned sodium, magnesium and ammonium salts. As the lower alkyl group may be mentioned, for example, methyl, ethyl, straight chain or branched propyl and butyl. The alkyl moiety of 2 to 11 carbon atoms can represent ethyl, straight chain and branched propyl, butyl, pentyl, hexyl, heptyl, octyl, nonyl, decyl and undecyl.

In a preferred aspect, the compound (I) has the following parameters:

c is one;

p and w are each one;

A preferred group of compounds (I) has the formula

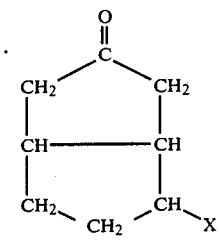
(II)

In this preferred group may be mentioned compounds, wherein X is: —$(CH_2)_4CH(OH)CH_2CH_3$, —$(CH_2)_4CH(OCH_3)CH_2CH_3$, —$(CH_2)_4CH(OCOCH_3)C_2H_5$, —$(CH_2)_5OCO-CH_3$, $(CH_2)_4COOCH_3$, —$(CH_2)_4CH(OCH_2CH_3)CH_2CH_3$, —$(CH_2)_4COCH_2CH_3$, and —$(CH_2)_4CH_2OH$, —$(CH_2)_6CH_3$, —$(CH_2)_2CH(OH)CH_2CH_3$, —$(CH_2)_2COCH_2CH_3$ —$(CH_2)_4CHO$ —$(CH_2)_4COOH$.

Particularly preferred are compounds of formula (II) which are 2-(5-substituted alkyl)bicyclo[3.3.0]octan-7-ones, including 2-(5-hydroxyhept-1-yl)bicyclo[3.3.0]octan-7-one {hexahydro-4-(5-hydroxyheptyl)-2 (1H)-pentalenone} (Compound IV), 2-(5-methoxyhept-1-yl)bicyclo [3.3.0]octan-7-one {hexahydro-4-(5-methoxyheptyl)-2(1H)-pentalenone} (Compound V), 2-(5-ethoxyhept-1-yl)bicyclo[3.3.0]octan-7-one 4-(5-ethoxyheptyl)hexahydro-2(1H)-pentalenone (Compound VI).

It has also been found that compounds of formula (I) above in which the oxygenated group Q is a member of a fused cyclobutane ring, are of great value. In a preferred embodiment, integer p is zero, thus establishing a bicyclo[3.2.0]heptan-7-one ring structure.

In certain preferred compounds a cis bridge (that is with the bridgehead protons presumably situated on the same side of the ring plane) and X-substituent of the type described above are present. Especially preferred are the compounds with a 2-X substituent on the second carbon of the formula:

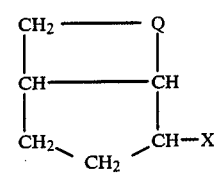
(III)

Compounds of formula (I) are present in the reaction mixture as isomers.

In the predominant alpha configuration (alternatively designated as exo), the bridgehead protons and the X-substituent are presumably situated on the same side of the ring plane. In the beta configuration (alternatively designated as endo), the bridgehead protons and the X-substituent are presumably situated on opposite sides of the ring plane.

In this preferred group there are especially preferred compounds with a cis bridge, the Q group being carbonyl and X being defined as in formulas I and II above. Also preferred are substituents in the 2-position of the formula $(CH_2)_m$-CH(OE)G, where E and G are H, methyl or ethyl; m is desirably four. The 2-carbon is the carbon in the lower ring adjacent to the bridgehead carbon adjacent to Q.

Also provided is an anti-androgenic composition suitable for providing an anti-androgenic effect when administered to a patient, which comprises a pharmaceutically effective amount of compounds (I) and a pharmaceutically acceptable carrier suitable for topical administration of the said compound as such pharmaceutically acceptable carrier may be mentioned an alcohol, salve, suspension, emulsion, ointment, cream, powder or spray. In a preferred embodiment, an alcohol such as ethanol and isopropanol are employed as pharmaceutically acceptable carriers.

The present compositions are particularly useful in treatment of acne, where the patient afflicted with acne is treated with compounds (I). This reduces androgen reaching androgen receptor sites, thereby alleviating the acne problem. The compounds (I) have a desirable effect in that, on topical administration, they will increase elastin and decrease collagen. In this aspect, the effect of compounds (I) resembles that of estrogen, but the estrogenic hormonal actions are avoided.

A further preferred embodiment provides compounds of type (I) for the prevention of keloids, wrinkling of the skin and related conditions. Extremely minute concentrations, even dilutions exceeding 100,000:1, are effective for these conditions.

Experiments generally following the methodology of Boote et al., *Biochimica et Biophysica Acta,* Volume 607, pages 145-160 (1980), have shown that while control human fibroblast cells have copious collagen production, treatment with the compounds of the invention provides human fibroblast cells with suppressed collagen production and with an about 30% increase in elastin production over control cells.

In a further preferred embodiment, the compounds (I) are provided in a sustained release composition for transdermal application to the skin of a patient. The sustained release composition should be one which will maintain the compounds (I) at the skin and permit release to the skin for a period of preferably at least about six to eight hours. An example of a sustained release composition is polyvinyl alcohol with a molecular weight of at least 8,000. For example, a polyvinyl alcohol having a molecular weight of about 20,000 is suitable for use with the compounds (I).

A further embodiment provides a skin composition suitable for topical administration to a patient to be exposed to ultraviolet light which includes both the compounds (I) and an ultraviolet screening agent such as para-aminobenzoic acid or cocoa butter.

A shampoo is advantageously provided for sufferers of skin problems and particularly, male pattern baldness, which comprises conventional shampoo ingredients having incorporated therein the compounds (I).

The invention provides a method of blocking androgen receptor sites in a patient which comprises introducing to said sites the compounds (I). Male pattern baldness, which is androgen linked, can be treated with these compounds to block androgen receptor sites.

While topical application of compounds (I) constitutes one embodiment of the invention, other routes for pharmaceutical administration are also contemplated, particularly the oral and suppository routes. Oral dosage unit formulations include tablets, capsules and other conventional oral forms. In a tablet the compounds are typically present in an amount of from about 1 to 50% by weight, with the inert carrier constituting the remainder of the tablet. Tablets are compressed in a conventional manner, with typically one percent magnesium stearate being included in the mixture to be tabletted. Liquid oral dosage unit formulations may also be used in which the compounds are incorporated into vehicles conventionally used for lipid soluble compounds. By including at least one carboxy or carboxy ester group in the compound, a hydrophilic character may be obtained. Suppositories with the compounds (I) are also contemplated, to provide a rectal suppository administration of the drug, which form takes advantage of the usual suppository ingredients.

The high potency of the compounds permits relatively low dosages both systemically, via oral or suppository routes, or through topical (transdermal) application. A concentration of the compounds of from about 0.001 to 5 percent by weight of the composition, and generally from about 0.01 to about one percent, is useful. Topical application on an infrequent basis, through a sustained release delivery, may indicate a relatively higher amount of the compounds, preferably in the range of from about 0.05 to about 3 percent by weight. A relatively lower concentration of the compounds is indicated where a larger surface area is treated, such as the back, chest, etc., e.g., a concentration of from about 0.01 to 1 percent by weight.

Where the compound is indicated for systemic delivery, oral, injection, suppository and sublingual forms may be used. Preferably the compound is administered as an oral dosage unit form, such as a tablet, capsule, powder or other traditional dosage unit form. In a preferred embodiment, the oral dosage unit form is a tablet which contains a relatively small amount of compounds (I), which is possible due to their high anti-androgenic potency. A single oral dosage unit formulation, is administered as one oral dosage unit formulation several times per day, in general up to about four times per day. For a normal adult male this comprises an amount of about 0.0001 to about 40 mg per oral dosage unit form, and preferably from about 0.01 to about 2 mg per oral dosage unit form.

It is to be understood that the extremely small amount of the compound necessary means as a practical matter that a "normal" tablet size will have only a very small percentage of the compound, with the remainder comprising pharmaceutically acceptable ingredients such as talcum, maize starch, polyvinyl pyrrolidone and lactose, together with a small amount of a tabletting agent such as magnesium stearate.

In a further preferred embodiment, the compounds (I) are provided in an oral dosage form for the treatment of arteriosclerosis. The systemic delivery of the compounds (I) to a patient is useful in order for the compound to reach the bloodstream to block collagen formation which would otherwise form sites for platelets. Avoidance of such collagen site formation thereby alleviates the spread of arteriosclerosis. While oral, injectable, suppository and sublingual forms may be used, the compounds (I) are advantageously administered as an oral dosage unit form.

A further aspect of the invention comprises a method of controlling a microorganism having androgen receptor sites by supplying to such androgen receptor sites an anti-androgenic agent, whereby androgen receptor sites are blocked, thereby retarding the delivery of androgens that would otherwise reach said receptor sites.

Pathogenic strains of Candida, Actinomyces, Norcardia, Cryptococci, Torulopsis, Aspergillus, Sporotrichum, Trichophyton, Blastomyces, Histoplasma, Microsporum and Coccidia have been analyzed for hormonal receptors. Estrogen, progesterone and androgen receptors were found in all strains of the above species.

Fermentation processes may be advantageously controlled by controlling the rate of fermentation with such fungi. Inhibition of zearalenone and zearalanol production by Fusarium fungi is a particular aspect of the invention, as well as inhibition of the adverse effects of zearalenone.

Use of bicyclo[3.2.0]heptan-7-ones of structure (III) is described herein for the preparation of intermediates in the production of hexahydro-2(1H)pentalen-2-ones of structure (I) above.

The general scheme for preparing the novel compounds comprises two phases. In one phase the ring structure is prepared, and in the other the side chain in the form of a precursor of the desired chain is prepared. The ring and side chain precursors are combined and subjected to further reactions to generate the desired products.

The following examples are given to demonstrate the compounds of the invention. For the sake of comprehension, two methods of nomenclature have been used in providing the name for each compound. The Chemical Abstract naming system directly follows the applicant's naming system where they differ. The Chemical Abstract name is set off by brackets { }.

EXAMPLE 1

3-(5-Methoxyhept-1-yl)cyclopentene

A three-neck, round-bottomed flask containing magnesium metal turnings (7.2 g, 0.299 moles), is equipped with a Friedrich condenser and kept under a nitrogen atmosphere. Tetrahydrofuran (300 ml) is added and the contents are allowed to stir. A solution of 1-chloro-5-methoxyheptane (48.1 g, 0.292 moles) is added in small portions and refluxed. The mixture is allowed to stir for 3 hours. The resultant dark yellow solution is cooled to −25° C., and the condenser is removed and replaced with a dry ice addition funnel. A solution of 3-chlorocyclopentene (29.9 g, 0.292 moles) is added over a period of one hour. The viscous solution is poured into two liters of saturated ammonium chloride, extracted with ether, and dried over anhydrous sodium sulfate. Distillation yields 3-(5-methoxyhept-1-yl)cyclopentene {3-(5-methoxyheptyl)cyclopentene} (51.5 g, 0.262 moles) as clear, colorless oil boiling at about 90° C. at 0.3 mm and 54° C. at 0.1 mm.

6,6-Dichloro-2-(5-methoxyhept-1-yl)bicyclo[3.2.0]heptan-7-one
{7,7-dichloro-4-(5-methoxyheptyl)bicyclo[3.2.0]heptan-6-one}

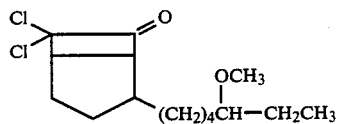

A 1,000 ml three-neck, round-bottomed flask, containing 3-(5-methoxyhept-1-yl)cyclopentene (15.0 g, 0.076 moles) in 300 ml of hexane, is equipped with a reflux condenser. Freshly distilled dichloroacetyl chloride (35.1 g, 0.240 moles) is added and the solution stirred and heated to reflux. Triethylamine (25.2 g, 0.249 moles) in 200 ml hexane, is added dropwise to the refluxing solution and the solution allowed to stir for 4 hours. The solvent is removed and the residue distilled and chromatographically purified with silica gel, leaving the product (17 g).

Analysis: IR: 2963, 2932, 2864, 2857, 2820, 1803, 1461, 1378, 1223, 1197, 1157, 1093, 1030, 968, 914, 842, 821, 802, 778, 740, and 673 cm$^{-1}$.

For the preparation of C$^{14}$-labeled 6,6-dichloro-2-(5-methoxyhept-1-yl)bicyclo[3.2.0]heptan-7-one {7,7-dichloro-4-(5-methoxyheptyl) bicyclo [3.2.0]heptan-6-one} C$^{14}$-labeled dichloroacetyl chloride is used.

6,6-Dichloro-2-(5-methoxyhept-1-yl)bicyclo[3.3.0]octan-7-one
{1,1-dichlorohexahydro-4-(5-methoxyheptyl)-2(1H)-pentalenone}

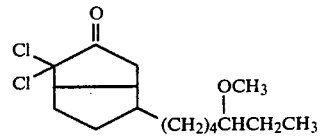

The starting material, 6,6-dichloro-2-(5-methoxyhept-1-yl) bicyclo[3.2.0]heptan-7-one {7,7-dichloro-4-(5-methoxyheptyl)bicyclo [3.2.0]heptan-6-one} (5 g), is dissolved in 100 ml of ether and transferred to a 500 ml, round-bottomed flask. An excess of diazomethane is generated in situ by reacting N-methyl-N-nitroso-p-toluene sulfonamide (60 g) with potassium hydroxide in ethanol. The diazomethane is allowed to react for 50 minutes, after which time acetic acid is added to destroy any remaining diazomethane. The solution is extracted with ether and dried over anhydrous sodium sulfate and yields the crude product as an orange oil.

2-(5-Methoxyhept-1-yl)bicyclo[3.3.0]octan-7-one(Compound V)
{hexahydro-4-(5-methoxyheptyl)-2(1H)-pentalenone}

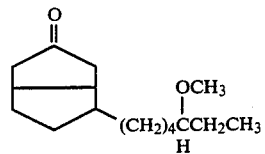

6,6-Dichloro-2-(5-methoxyhept-1-yl)bicyclo[3.3.0]octan-7-one {1,1-dichlorohexahydro-4-(5-methoxyheptyl)-2(1H)-pentalenone} (45.9 g) is added to a 100 ml, round-bottomed flask fitted with a condenser. Powdered zinc metal (92 g) and glacial acetic acid (312 ml) are added to the flask and the solution allowed to reflux for an hour. The solution is filtered to remove the zinc and zinc chloride, formed in the reaction. The product is washed with an aqueous sodium bicarbonate solution and extracted three times with ether. The ether extracts are combined and dried over anhydrous sodium sulfate. The resulting yellow oil is chromatographed on silica gel and eluted with 4:1 hexane:ether. The fractions are combined, and gave 2-(5-methoxyhept-1-yl)bicyclo [3.3.0]octan-7-one {hexahydro-4-(5-methoxyheptyl)-2(1H)-pentalenone} as a clear, colorless oil.

Analysis: IR: 2928, 2853, 2828, 1740, 1460, 1402, 1735, 1158, 1122, 1093, 1050, 1035, 960, and 740 cm$^{-1}$.

EXAMPLE 1A (Alternate Preparation of Compound V)

Synthesis of 3-(5-methoxyhept-1-yl)cyclopentene 3-(5-Hydroxyhept-1-yl)cyclopentene {alpha-ethyl-2-cyclopentene-1-pentanol} (10 g, 0.054 moles) is added to a solution containing potassium hydroxide (12.3 g, 0.219 moles) partially dissolved in dimethyl sulfoxide (108 ml). The reaction is stirred and methyl iodide (15.3 g, 0.108 moles) is added rapidly.

The solution is heated in a 30° C. water bath for 12 hours, after which time the reaction is poured into water (200 ml) and partitioned with methylene chloride. The aqueous phase is extracted with methylene chloride (2×100 ml) and the extracts are combined and dried over anhydrous sodium sulfate. The solvent is removed under vacuum leaving a clear yellow oil. The crude product is fractionally distilled under reduced pressure leaving a clear, colorless oil (7.4 g, 0.038 moles), BP 65° C./0.1 mm.

Analysis: IR: 3047, 2927, 2850, 2818, 1459, 1359, 1154, 1093, and 716 cm$^{-1}$.

6,6-Dichloro-2-(5-methoxyhept-1-yl)bicyclo[3.2.0]heptan-7-one
{7,7-dichloro-4-(5-methoxyheptyl)bicyclo[3.2.0]heptan-6-one} and
7,7-dichloro-2-(5-methoxyhept-1-yl)bicyclo[3.2.0]heptan-6-one
{7,7-dichloro-2-(5-methoxyheptyl)bicyclo[3.2.0]heptan-6-one}

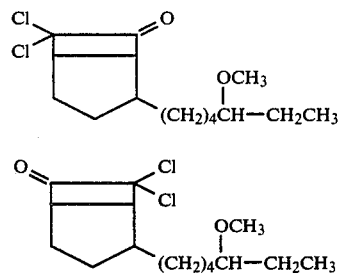

The procedure followed is the same as that described in Example 9 substituting the starting material, 3-(5-methoxyhept-1yl)cyclopentene (7.4 g, 0.038 moles), trichloroacetyl chloride (6.9 g, 0.038 moles), and phosphorous oxchloride (5.8 g, 0.038 moles). The crude product is kugelrohred and fractionally distilled under reduced pressure leaving a clear, colorless oil (8.1 g, 0.026 moles), BP 138° C./0.1 mm.

Analysis: IR: 2963, 2932, 2864, 2857, 2820, 1803, 1461, 1378, 1223, 1197, 1157, 1093, 1030, 968, 914, 842, 821, 802, 778, and 673 cm$^{-1}$.

EXAMPLE 1B

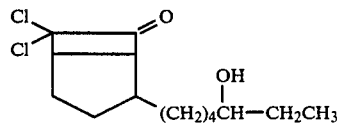

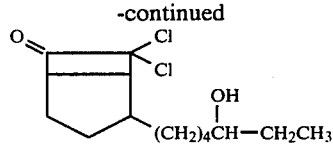

Alpha and beta isomers of
6,6-dichloro-2-(5-hydroxyhept-1-yl)bicyclo[3.2.0]heptan-7-one
{7,7-dichloro-4-(5-hydroxyheptyl)bicyclo[3.2.0]heptan-6-one} and
7,7-dichloro-2-(5-hydroxyhept-1-yl)bicyclo[3.2.0]heptan-6-one
{7,7-dichloro-2-(5-hydroxyheptyl)bicyclo[3.2.0]heptan-6-one}

A mixture of the isomers of dichloro-2-(5-methoxyhept-1-yl)bicyclo[3.2.0]heptanone (30.6 g) obtained as in Example 1A, sodium iodide (31.4 g) and trimethylsilyl chloride (11.4 g moles) are added to a solution of acetonitrile (140 ml). The solution is stirred under an inert atmosphere for four hours after which time 50 ml water is added until the solution changes to a clear red color. The mixture is extracted with diethyl ether (150 ml) and the aqueous phase is discarded. The ether phase is washed with solutions of saturated sodium thiosulfate (75 ml) and brine (100 ml). The solvent is removed under vacuum leaving a clear, light yellow oil. The crude product contains a mixture of the starting material, the desired alcohols, and by-products. This mixture is purified by silica gel chromatography using a 4:1 hexane-ether (v/v) solution. Vacuum distillation at 0.1 mm pressure and about 130° C. yields a mixture of the alpha and beta isomers of 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one} and 7,7-dichloro-2-(5-hydroxyhept-1-yl]bicyclo[3.2.0]heptan-6-one {7,7-dichloro-2-(5-hydroxyheptyl) bicyclo[3.2.0]heptan-6-one}. Infrared absorption maxima are observed at 3584, 3534, 3389, 3377, 2959, 2934, 2871, 2856, 1804, 1462, 1409, 1378, 1337, 1317, 1301, 1279, 1252, 1250, 1245, 1180, 1159, 1134, 1119, 1090, 1031, 965, 923, 896, 864, 811, 779, 742 and 676 cm$^{-1}$.

Separation of Isomers

Identification and separation of the three principal isomers can be accomplished by use of a Beckman high performance liquid chromatograph equipped with a 165 variable wavelength detector. A Beckman 15 cm C-18 column with 5 micron packing was used for all analytical determinations. A 60%:40% acetonitrile:water solvent is used with a flow rate of 1 ml/min. The detector has wavelength scanning capabilities making it possible to determine the lambda maximum of these isomers. All three major peaks detected by the system had identical UV scans from 200–350 lambda with a lambda max 1 of 213 nm and a lambda max 2 of 319 nm, consistent with a carbonyl group in the chemical structure.

Separation of the isomers is accomplished using a Watman Magnum 20 column with 50 micron packing of C-18. A 0.5 g sample of the isomeric mixture is dissolved in 1.5 ml of acetonitrile. A 60%:40% acetonitrile:water solvent system is used with a flowrate of 20 ml/min. The detector monitors the samples at 210 and 318 nm. A total of 80 tubes (10 ml each) was collected and the samples were analyzed for the desired isomers by capillary gas chromatography. The appropriate tubes were then pooled together and the acetonitrile removed under vacuum. The aqueous phase was extracted with ether and the solvent again removed under vacuum and dried over anhydrous sodium sulfate, leaving clear yellow oils of 0.2 g of alpha 6,6-dichloro-2-(5-hydroxyhept-1-yl)bicyclo [3.2.0]heptan-7-one {7,7-dichloro-4-(5-hydroxyheptyl)bicyclo [3.2.0]heptan-6-one} and 0.1 g of alpha 7,7-dichloro-2-(5-hydroxyhept-1-yl)bicyclo[3.2.0.]heptan-6-one {7,7-dichloro-2-(5-hydroxyheptyl) bicyclo[3.2.0]heptan-6-one}.

The alpha 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one} gives the following key NMR resonances: 1H, 3.82, doublet (1H), 3.53 multiplet (1H), 3.37 (d of d) 1H, 2.40 quartet (1H), 0.944 triplet (3H).

In the case of the alpha 7,7-dichloro compound, the following NMR regions were noted:

1H 4.03 d of d (1H), 3.53 multiplet (1H), 3.07 doublet (1H), 240 quartet (1H) and 0.948 triplet (3H).

Besides the alpha 7,7-dichloro compounds, smaller quantities of beta isomers are eluted. The following NMR resonances are noted 3.94 d of d (1H), 3.53 multiplet (1H), 3.42 d of d (1H), 0.94 triplet (3H).

The alpha 6,6-dichloro-2-(5-hydroxyhept-1-yl)bicyclo-[3.2.0]heptan-7-one {7,7-dichloro-4-(5-hydroxyheptyl)bicyclo[3.2.0]heptan-6-one} can also be obtained from the mixture of alpha and beta 6,6-dichloro and 7,7-dichloro isomers by applying the crude mixture directly on a flash chromatography column (e.g. 2.5 cm diameter, 200–430 mesh) and eluting with a 6:1 hexane-ether (v/v) solution, collecting fractions in 20 ml tubes. The presence of the alpha 6,6-dichloro product in tubes can be determined by gas chromatography by comparison with the pure alpha 6,6-dichloro product obtained above using high performance liquid chromatography.

EXAMPLE 2

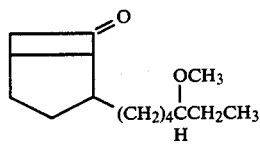

2-(5-Methoxyhept-1-yl)bicyclo[3.2.0]heptan-7-one {4-(5-methoxyheptyl) bicyclo [3.2.0]heptan-6-one}

Zinc (4 g) is added to a stirred solution of 6,6-dichloro-2-(5-methoxyhept-1yl)bicyclo[3.2.0]heptan-7-one {7,7-dichloro-4-(5-methoxyheptyl)bicyclo[3.2.0-]heptan-6-one} (2 g) in glacial acetic acid (120 ml).

The solution is stirred at room temperature for one hour, then refluxed for 1 hour, after which time the mixture is filtered through a sintered glass funnel and the ether solution dried over anhydrous sodium sulfate. The solvent is removed under vacuum, leaving the crude product. Chromatography on silica gel yields 2-(5-methoxyhept-1-yl)bicyclo[3.2.0]heptan-7-one {4-(5-methoxyheptyl)bicyclo[3.2.0]heptan-6-one} (1.2 g).

Analysis: IR: 2959, 2933, 2859, 2820, 1778, 1461, 1406, 1386, 1316, 1303, 1260, 1236, 1197, 1154, 1091, 1024, 921, 862, and 819 cm$^{-1}$.

EXAMPLE 3

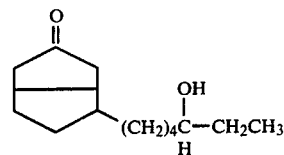

2-(5-Hydroxyhept-1-yl)bicyclo[3.3.0]octan-7-one {hexahydro-4-(5-hydroxyheptyl)-2(1H)-pentalenone} (Compound IV)

Sodium iodide (3 g) is added to a solution of 1 g of 2-(5-methoxyhept-1-yl)bicyclo[3.3.0]octan-7-one{hexahydro-4-(5-methoxyheptyl)-2(1H)-pentalenone} in 20 ml of acetonitrile. The resultant red solution is stirred at room temperature and 2.5 ml of trimethylsilyl chloride is added. After 7.5 hours, water is added, followed by a saturated aqueous sodium thiosulfate solution. The solvent is removed under vacuum, leaving a light yellow oil. Chromatography on silica gel leaves pure 2-(5-hydroxyhept-1-yl)bicyclo[3.3.0]octan-7-one {hexahydro-4-(5-hydroxyheptyl)-2(1H)-pentalenone}.

Analysis: IR: 3395, 2935, 2855, 1748, 1465, 1267, 1245, 1160, 1120, 965, 920, 810, 785, and 745 cm$^{-1}$.

EXAMPLE 4

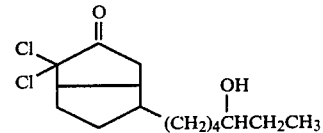

6,6-Dichloro-2-(5-hydroxyhept-1-yl)bicyclo[3.3.0]octan-7-one
{1,1-dichlorohexahydro-4-(5-hydroxyheptyl)-2(1H)-pentalenone}

Using the demethoxylation procedure of the previous example on 6,6-dichloro-2-(5-methoxyhept-1-yl)bicyclo-[3.3.0]octan-7-one {1,1-dichlorohexahydro-4-(5-methoxyheptyl)-2(1H)-pentalenone} the 5-hydroxyheptyl derivative was obtained.

Analysis: IR: 3416, 2955, 2868, 2856, 1801, 1462, 1131, 1118, 1029, 987, 967, 741, and 675 cm$^{-1}$.

Demethoxylation of 6,6-dichloro-2-(5-methoxyhept-1-yl)bicyclo[3.2.0]heptan-7-one {7,7-dichloro-4-(5-methoxyheptyl)bicyclo[3.2.0]heptan-6-one} produces 6,6-dichloro-2-(5-hydroxyhept-1yl)bicyclo[3.2.0]heptan-7-one {7,7-dichloro-4-(5-hydroxyheptyl)bicyclo [3.2.0]heptan-6-one}.

The corresponding 2-(5-ethoxyhept-1-yl) homologs are prepared by substituting an equivalent amount of 1-chloro-5-ethoxyheptane in the Grignard reaction of Example 1 in place of the 5-methoxy homolog and using the reaction sequence shown above to prepare first the 3-(5-ethoxyhept-1-yl)cyclopentene, which is then converted to the 6,6-dichloro-2-(5-ethoxyhept-1-yl)bicyclo[3.2.0]heptan-7-one {7,7-dichloro-4-(5-ethoxyheptyl)bicyclo[3.2.0]heptan-6-one} of this invention. The diazomethane reaction described for the methoxy homolog produces the 6,6-dichloro-2-(5-ethoxyhept-1yl) bicyclo[3.3.0]octan-7-one {7,7-dichloro-4-(5-ethoxyheptyl)bicyclo[3.2.0]heptan-6-one}.

The two vicinal chlorine atoms can be removed from the aforementioned 6,6-dichloro derivatives by the above described method of treatment with zinc in glacial acetic acid to produce the 2-(5-ethoxyhept-1-yl)bicyclo[3.2.0]heptan-7-one {4-(5-ethoxyheptyl)bicyclo[3.2.0]heptan-6-one} and the 2-(5-ethoxyhept-1-yl)bicyclo[3.3.0]octan-7-one {4-(5-ethoxyheptyl)hexahydro-2(1H)-pentalenone} (Compounds VI) respectively.

Analysis: IR: 2964, 2930, 2859, 1741, 1461, 1404, 1369, 1343, 1300, 1241, 1152, 1109, 1080, 875 and 797 cm$^{-1}$.

EXAMPLE 4A (Alternate Preparations)

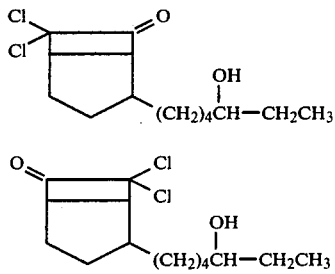

Alpha and beta isomers of 6,6-dichloro-2-(5-hydroxyhept-1-yl)bicyclo[3.2.0]heptan-7-one{7,7-dichloro-4-(5-hydroxyheptyl)bicyclo[3.2.0]heptan-6-one} and 7,7-dichloro-2-(5-hydroxyhept-1-yl)bicyclo[3.2.0]heptan-6-one {7,7-dichloro-2-(5-hydroxyheptyl)bicyclo[3.2.0]heptan-6-one}

The procedure followed is the same as that described in Example 12 substituting the starting material from Example 16, 6,6-dichloro-2-(5-[(1,1-dimethylethyl)-dimethylsiloxy]hept-1-yl)bicyclo[3.2.0]heptan-7-one {7,7-dichloro-4-[5-[[(1,1-dimethylethyl)dimethylsilyl]oxy]bicyclo[3.2.0]heptan-6-one]} and isomers (21.8 g, 0.053 moles), acetonitrile (436 ml), and 40% hydrofluoric acid (22 ml). The crude product is chromatographed on silica gel and subsequently kugelrohred under vacuum leaving a clear, colorless oil (12.5 g, 0.475 moles).

Analysis 3408 (broad), 2959, 2935, 2874, 2860, 1804, 1463, 1455, 1445, 1376, 1319, 1304, 1281, 1250, 1247, 1225, 1159, 1135, 1116, 1090, 1065, 1031, 966, 924, 865, 855, 844, 811, 780, 742, and 675 cm$^{-1}$.

Alpha and beta isomers of 6,6-dichloro-2-(5-ethoxyhept-1-yl)bicyclo[3.2.0]heptan-7-one {7,7-dichloro-4-(5-ethoxyheptyl)bicyclo[3.2.0]heptan-6-one} and 7,7-dichloro-2-(5-ethoxyhept-1-yl)bicyclo[3.2.0]heptan-6-one {7,7-dichloro-2-(5-ethoxyheptyl)bicyclo[3.2.0]heptan-6-one}

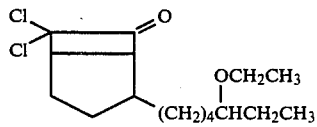

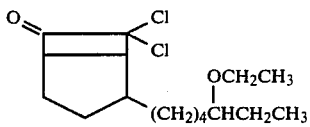

The procedure followed is the same as that described in Example 9 substituting the starting material prepared in Example 39, 3-(5-ethoxyhept-1-yl)cyclopentene {3-(5-ethoxyheptyl)cyclopentene} (170 g, 0.573 moles) dissolved in ether (1700 ml), trichloroacetyl chloride (187 g, 1.03 moles), phosphorous oxychloride (158 g, 1.03 moles) both dissolved in ether (500 ml), and zinc/copper couple (75 g, 1.15 moles) are used. The crude product is kugelrohed and subsequently fractionally distilled under reduced pressure leaving a clear, colorless oil (108 g, 0.338 moles), BP 145° C./0.31 mm.

Analysis: IR: 2965, 2931, 2862, 1803, 1480, 1461, 1450, 1400, 1370, 1345, 1225, 1107, 1080, 1028, 970, 822, 800, 738, 725, 670, and 654 cm$^{31\ 1}$.

EXAMPLE 4B

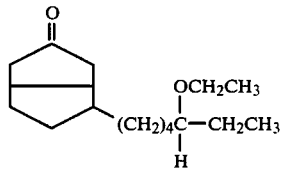

Alpha and beta isomers of 2-(5-ethoxyhept-1-yl)bicyclo[3.3.0]octan-7-one {4-(5-ethoxyheptyl)hexahydro-2(1H)-pentalenone}

Diazomethane is generated in situ from N-methyl-N-nitroso-p-toluenesulfonamide (60 g, Diazald) using the macro diazald kit (Aldrich). 6,6-Dichloro-2-(5-ethoxyhept-1-yl)bicyclo[3.2.0]heptan-7-one {7,7-dichloro-4-(5-ethoxyheptyl)bicyclo[3.2.0]heptan-6-one} and isomers (36 g, 0.113 moles) is treated with an etheral diazomethane solution (100 ml) followed by methanol (4 ml).

After 50 minutes the excess diazomethane is neutralized with the addition of acetic acid (10 ml). The solvent is removed under vacuum leaving a clear yellow liquid. The crude product is then diluted with acetic acid (240 ml) and stirred while zinc powder (72 g, 1.10 moles) is slowly added. The reaction is heated in a 70° C. water bath for 1 hour, after which time ether (500 ml) is added and the solution filtered. The ether layer is washed with brine (100 ml) and then with a solution of saturated bicarbonate. The ether layer is separated and dried over sodium sulfate. The solvent is removed under vacuum leaving a clear yellow oil. The crude 2-(5-ethoxyhept-1-yl)bicyclo[3.3.0]octan-7one {hexahydro-4-(5-methoxyheptyl)-2(1H)-pentalenone} is chromatographed on silica gel and subsequently kugelrohred under vacuum leaving compound VI as a clear, colorless oil (12 g, 0.045 moles).

EXAMPLE 5

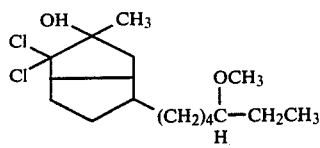

Alpha and beta isomers of 2-(5-Methoxyhept-1-yl)-7-methyl-bicyclo[3.3.0]octan-7-ol {1-dichlorooctahydro-4-(5-methoxyheptyl)-2-methyl-2pentalenol}

6,6-Dichloro-2-(5-methoxyhept-1-yl)bicyclo[3.3.0]octan-7- one {1,1-dichlorohexahydro-4-(5-methoxyheptyl)-2(1H)-pentalenone} (4 g, 0.0158 moles) is added to a 400 ml ether solution of diazomethane, generated from 45 g of N-methyl-N-nitroso p-toluenesulfonamide. The reaction is allowed to proceed for 5 hours after which glacial acetic acid is added dropwise to neutralize the excess diazomethane. The ether solution is washed with sodium bicarbonate and dried over anhydrous sodium sulfate. The solvent is removed under vacuum, leaving an orange oil. This oil is applied in hexane and ether to a silica gel chromatography column and elution with 4:1 hexane-ether yields the product as a clear liquid. Infrared maxima are observed at 3430, 2931, 2856, 1658, 1461, 1379, 1362, 1328, 1325, 1316, 1244, 1195, 1173, 1162, 1093, 1027, 984, 950, and 923 cm$^{-1}$. Substitution in this reaction of 6,6-dichloro-2-(5-hydroxyhept-1-yl)bicyclo[3.3.0]octan-7-one {1,1-dichlorohexahydro-4-(5-hydroxyheptyl)-2(1H)-pentalenone} leads to the corresponding 6,6-dichloro-2-(5-hydroxyhept-1-yl)7-methylbicyclo [3.3.0]octan-7-ol {4,4-dichloro-alpha-ethyloctahydro-5-hydroxy-5-methyl-1-pentalenepentanol}.

2-(5-Methoxyhept-1-yl)bicyclo[3.3.0]octan-7-one {hexahydro-4-(5-methoxyheptyl)-2(1H)-pentalenone} (4 g, 0.0158 moles) diluted in ether is added dropwise to a stirring solution of ethyl magnesium bromide (0.0158 moles) dissolved with diethyl ether. The mixture is cooled in an ice bath during the addition. The ice bath is removed and the solution stirred for an additional hour. The reaction is quenched with water and a 15% sulfuric acid solution. The organic phase is separated and the solvent removed under vacuum. The aqueous layer is extracted with ether (2×200 ml) and the extracts are combined with the organic layer and dried over anhydrous sodium sulfate. The solid is filtered off and the remaining solvent removed leaving a clear, pale yellow oil. The crude product is subsequently chromatographed on silica gel yielding desired product as a clear colorless oil (1.7 g, 6.3 mmoles).

Analysis: IR: 3424 (broad), 2933, 2855, 2820, 1461, 1370, 1309, 1299, 1262, 1197, 1148, 1095, 949 and 920 cm$^{-1}$. An equivalent amount of methyl magnesium bromide can be used to make the 7-methyl homolog.

EXAMPLE 6

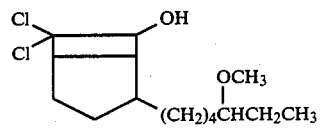

Alpha and beta isomers of 6,6-dichloro-2-(5-methoxyhept-1-yl) bicyclo[3.2.0]heptan-7-ol {7,7-dichloro-4-(5-methoxyheptyl)bicyclo[3.2.0]heptan-6-ol} and 7,7-dichloro-2-(5-methoxyhept-1-yl) bicyclo[3.2.0]heptan-6-ol {7,7-dichloro-2-(5-methoxyheptyl)bicyclo[3.2.0]heptan-6-ol}

Sodium borohydride (0.2 g) was added in one portion. To a solution of 50 ml of ethanol, 30 ml of water, and 8 g of sodium hydroxide, 6,6-dichloro-2-(5-methoxyheptyl)bicyclo[3.2.0]heptan-7-one {7,7-dichloro-4-(5-methoxyheptyl)bicyclo[3.2.0]heptan-6-one} (1 g) is added and the reaction mixture is heated at 45° C. for 10 hours. The solution is then cooled in an ice bath and concentrated hydrochloric acid is added dropwise until the solution has reached a pH of 7. The solution is then extracted with ether (3×75 ml) and the ether extracts are combined and washed with aqueous sodium bicarbonate and dried over anhydrous sodium sulfate. The solvent is removed under vacuum, leaving 0.4 g of a clear yellow product.

Analysis: IR: 3501, 2960, 2932, 2856, 2822, 1461, 1374, 1261, 1248, 1239, 1161, 1132, 1093, 1037, 998, 963, 943, 750, 724, 690 cm$^{-1}$.

Treatment of the product with zinc as described above yields 2-(5-methoxyheptyl)bicyclo[3.2.0]heptan-7-ol {4-(5-methoxyheptyl) bicyclo[3.2.0]heptan-6-one}.

The reactions of this example can also be conducted using an equivalent amount of 6,6-dichloro-2-(5-methoxyhept-1-yl)bicyclo [3.3.0]octan-7-one {1-1-dichlorohexahydro-4-(5-methoxyheptyl)-2 (1H)-pentalenone} to first prepare 6,6-dichloro-2-(5-methoxyhept-1-yl) bicyclo[3.3.0]octan-7-ol {1,1-dichlorooctahydro-4-(5-methoxyheptyl)-2-pentalenol} which is then treated by the zinc in glacial acetic acid to produce 2-(5-methoxyhept-1-yl)bicyclo [3.3.0]-octan-7-ol {octahydro-4-(5-methoxyheptyl)-2-pentalenol}.

Analysis: IR: 3501 (broad), 2960, 2932, 2856, 2822, 2736, 1657, 1638, 1635, 1461, 1374, 1303, 1261, 1248, 1246, 1239, 1161, 1132, 1093, 1037, 998, 963, 943, 920, 750, 724, 690 cm$^{-1}$.

EXAMPLE 7

(5-Chloro-1-pentyloxy)(2,2-dimethylethyl)dimethylsilane

{[(5chloropentyl)oxy](1,1-dimethylethyl)dimethylsilane}

5-Chloropentanol (325 g, 2.65 moles) is added to a solution containing tert-butyldimethylsilyl chloride (439 g, 2.91 moles) and dimethylformamide (1.625 liters). The solution is stirred and imidazole (199 g, 2.91 moles) is added at once. The solution is stirred at room temperature for 6 hours, after which time water (1 liter) is added and the reaction is partitioned with hexanes. The organic phase is separated and the solvent volume reduced under vacuum. The residue is dried over anhydrous magnesium sulfate and the remaining solvent removed under vacuum, leaving a clear, colorless oil.

The crude product is subsequently fractionally distilled under reduced pressure leaving the product as a clear, colorless oil (534 g, 2.26 moles), BP 71° C./0.3 mm.

Analysis: IR: 2958, 2930, 2898, 2862, 2802, 2739, 1472, 1463, 1447, 1434, 1407, 1389, 1361, 1353, 1291, 1257, 1218, 1153, 1106, 1055, 1031, 1024, 1007, 983, 939, 928, 913, 836, 813, 776, 727, 678, and 657 cm$^{-1}$.

Although, t-butyl dimethylsilylchloride was used as a protecting group, a variety of hydroxyl protecting groups may be used.

EXAMPLE 8

3-(5-[(1,1-Dimethylethyl)dimethylsiloxy]pent-1-yl)cyclopentene
{[5-(2-cyclopenten-1-yl)pentyl](1,1-dimethylethyl)-dimethylsilane}

All reactions are carried out under an inert atmosphere. The starting material, (5-chloro-1-pentyloxy)(2,2-dimethylethyl) dimethylsilane {[(5-chloropentyl)oxy](1,1-dimethylethyl)dimethylsilane} (534 g, 2.26 moles), diluted in tetrahydrofuran (500 ml), is added portionwise to a refluxing solution of tetrahydrofuran and granular magnesium (75 g). After the addition is complete the reaction is refluxed an additional 2 hours and the resultant Grignard salt is cooled to room temperature, cannulated into a three liter flask, and cooled to −20° C. A solution of Li$_2$CuCl$_4$ (6.4 mmoles) is added, followed by the dropwise addition of 3-chlorocyclopentene (219 g, 2.1 moles) cooled in a −20° C. dry ice/ethanol bath. After the addition is complete the mixture is warmed to room temperature. Water (500 ml) is added. The reaction mixture is extracted with hexane (3×400 ml). The organic layers are combined, washed with brine (2×500 ml) and dried over anhydrous sodium sulfate. The remaining solvent is removed under vacuum leaving a clear yellow oil. The crude product is fractionally distilled under reduced pressure leaving a clear, colorless oil (478 g, 1.78 moles), BP 96° C./0.3 mm.

Analysis: IR: 3049, 2948, 2928, 2854, 1469, 1460, 1387, 59, 1254, 1103, 1052, 1027, 1005, 938, 834, 811, 773, 715, 676, and 661 cm$^{-1}$.

EXAMPLE 9

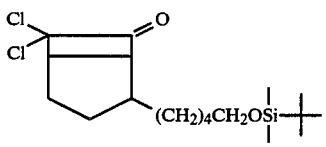

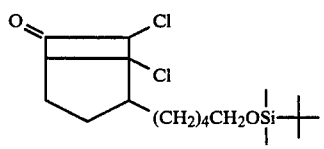

Alpha and beta isomers of
6,6-dichloro-2-(5-[(1,1-dimethyl-ethyl)dimethylsiloxy]pent-1-ylbicyclo[3.2.0]heptan-7-one
{7,7-dichloro-4-[5-[[(1,1-dimethylethyl)dimethylsilyl]oxy]pentyl]bicyclo[3.2.0]heptan-6-one} and
7,7-dichloro-2-(5-[(1,1-dimethylethyl)dimethylsiloxy]-pent-1-yl)bicyclo[3.2.0]heptan-6-one
{7,7-dichloro-2-[5[[(1,1-dimethylethyl)dimethylsilyl]oxy]pentyl]bicyclo[3.2.0]heptan-6-one}

A solution containing trichloroacetyl chloride (149 g, 0.82) and phosphorous oxychloride (126 g, 0.82 mole) dissolved in ether (600 ml) is added dropwise to a reaction vessel containing zinc (54 g, 0.82 moles), 3-(5-[(1,1,dimethylethyl)dimethylsiloxy]-pent-1-yl)cyclopentene (200 g, 0.745 moles), and ether (2 liter). After the addition is complete the reaction is refluxed for 4 hours. The reaction vessel is cooled to room temperature and the mixture neutralized by adding it to a saturated solution of sodium bicarbonate. The solution is filtered, the phases separated, and the aqueous layer is extracted with ether (2×1000 ml). The organic phases are combined and dried over anhydrous sodium sulfate. The solvent is removed under vacuum leaving a clear yellow oil. The crude product is kugelrohred and then fractionally distilled under vacuum leaving the product as a clear, colorless oil (148 g, 0.392 moles), BP 178° C./0.25 mm.

Analysis: IR: 2950, 2929, 2897, 2855, 1804, 1460, 1447, 1405, 1386, 1359, 1301, 1271, 1254, 1223, 1185, 1157, 1100, 1057, 1029, 1005, 974, 962, 937, 923, 901, 835, 813, 774, 741, and 673 cm$^{-1}$.

EXAMPLE 10

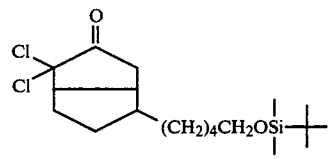

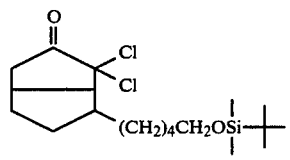

Alpha and beta isomers of
6,6-dichloro-2-(5-[(1,1-dimethylethyl)dimethylsiloxy]-pent-1-ylbicyclo[3.3.0]octan-7-one
{1,1-dichloro-4-[5-[[(1,1-dimethylethyl)dimethylsilyl]oxy]pentyl]hexahydro-2 (1H)-pentalenone} and
7,7-dichloro-2-(5-[(1,1-dimethylethyl)dimethylsiloxy]-pent-1-yl)bicyclo[3.3.0]octan-6-one
{1,1-dichloro-6[5-[[(1,1-dimethylethyl)dimethylsilyl]oxy]pentyl]hexahydro-2 (1H)-pentalenone}

Diazomethane is generated in situ from N-methyl-N-nitroso-p-toluenesulfonamide (60 g, 0.28 moles) according to the standard procedure using the macro diazald kit (Aldrich). The starting material 6,6-dichloro-2-(5-[(1,1,-dimethylethyl)dimethylsiloxy]pent-1-yl)bicyclo[3.2.0]heptan-7-one {7,7-dichloro-4-[5-[[(1,1-dimethylethyl)dimethylsilyl]oxy]pentyl]bicyclo[3.2.0]heptan-6-one} (30 g) is treated with diazomethane in 400 ml of ether and then with methanol (4 ml). After 50 minutes, the excess diazomethane is neutralized by the slow addition of glacial acetic acid (15 ml). The reaction mixture is neutralized with a solution of saturated sodium bicarbonate and then dried over anhydrous sodium sulfate. The solvent is removed under vacuum leaving a clear, yellow oil. The crude product is chromatographed on silica gel leaving a clear, colorless oil (12.1 g, 0.30 moles).

Analysis: IR: 2949, 2928, 2853, 1768, 1468, 1460, 1403, 1386, 1358, 1254, 1187, 1099, 1005, 979, 937, 919, 890, 834, 810, 774, 710, 658, and 633 cm$^{-1}$.

EXAMPLE 11

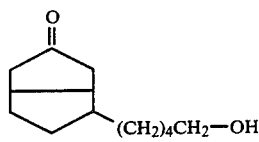

Alpha and beta isomers of
2-(5-hydroxypent-1-yl)bicyclo-[3.3.0]octan-7-one
{hexahydro-4-(5-hydroxypentyl)-2(1H)-pentalenone}

The starting material, 6,6-dichloro-2-(5-[(1,1-dimethylethyl)dimethylsiloxy]pent-1-yl)bicyclo[3.3.0]octan-7-one {1,1-dichloro-4-[5-[[(1,1-dimethylethyl)dimethylsilyl]oxy]pentyl]hexahydro-2(1H)-pentalenone}(12.1 g, 0.30 moles) is dissolved in glacial acetic acid (85 ml) and the solution is stirred while zinc (25 g) is slowly added. The reaction is heated at 70° C. for 1 hour, after which time ether (100 ml) is added and the solution filtered. The filtrate is washed with brine and then neutralized with saturated sodium bicarbonate. The ether layer is separated and dried over anhydrous sodium sulfate. The solvent is removed under vacuum leaving a clear yellow oil. The crude product is chromatographed on silica gel and subsequently kugelrohred under vacuum leaving a clear, colorless oil (0.72 g, 3.4 mmoles).

Analysis: IR: 3441, 2925; 2854, 1736, 1460, 1402, 1255, 1162, 1085, and 1065 cm$^{-1}$.

EXAMPLE 12

3-(5-Hydroxypent-1-yl)cyclopentene
{2-cyclopentene-1-pentanol}

3-(5-[(1,1-Dimethylethyl)dimethylsiloxy]pent-1-yl)cyclopentene (300 g, 1.170 moles) is diluted with acetonitrile (3000 ml) and a 40% stock solution of hydrofluoric acid (166 ml) is added. The reaction is stirred at room temperature for 10 minutes and then slowly neutralized with a saturated solution of sodium bicarbonate. The reaction is partitioned between ether (1500 ml) and the aqueous phase extracted with ether (1×1000 ml). The organic layers are combined and the solvent volume is reduced under vacuum. The residue is dried over anhydrous sodium sulfate and the remaining solvent removed leaving a clear, colorless oil. The product is kugelrohred under vacuum leaving a product sufficiently pure for the next reaction (171 g, 1.11 moles).

Analysis: IR: 3382 (broad), 3052, 2934, 2856, 1462, 1440, 1373, 1057, 1016, 717, 673, 663 cm$^{-1}$.

EXAMPLE 13

3-(Cyclopenten-3-yl)valeraldehyde
{2-cyclopentene-1-pentanal}

Pyridinium dichromate (621 g, 1.65 moles) is added to a solution of 3-(5-hydroxypent-1-yl)cyclopentene {2-cyclopentene-1-pentanol} (170 g, 1.10 moles) dissolved in methylene chloride (1552 ml). The solution is stirred at room temperature for 12 hours after which time isopropanol is added and the reaction stirred for 1 hour. The reaction is filtered through a pad of activated magnesium silicate (Florisil) and the solid rinsed with several portions of methylene chloride (3×400 ml). The solvent is removed under vacuum leaving a clear yellow oil. The crude product is kugelrohred under vacuum leaving clear, colorless oil (63 g, 0.414 moles).

Analysis: IR: 3052, 2934, 2854, 2719, 1731, 1462, 1442, 1411, 1392, 1361, 1285, 1260, 1178, 1166, 1150, 1091, 1055, 1034, 1007, 912, 719, and 612 ch$^{-1}$.

EXAMPLE 14

3-(5-Hydroxyhept-1-yl)cyclopentene
{alpha-ethyl-2-cyclopentene-1-pentanol}

All work is performed in an inert atmosphere using anhydrous tetrahydrofuran. The starting material, 3-(5-cyclopenten-3-yl) valeraldehyde {2-cyclopentene-1-pentanal} (75 g, 0.493 moles) is dissolved in tetrahydrofuran (750 ml) and cooled in a −30° C. ethanol/dry ice bath. Ethyl magnesium bromide (0.493 moles) is added dropwise to the stirring reaction mixture for a period of over 2 hours. The reaction is warmed to 0° C. and water (100 ml), followed by 15% sulfuric acid (200 ml), is added. The aqueous layer is extracted with ether (2×300 ml) and the organic extracts are combined, reduced in volume and washed with brine (400 ml). The product is dried over anhydrous sodium sulfate and the remaining solvent removed under vacuum leaving a clear yellow oil. The crude product is chromatographed on silica gel and subsequently kugelrohred under vacuum leaving clear, colorless oil (10.2 g, 0.056 moles).

Analysis: IR: 3387 (broad), 3054, 2930, 2875, 2857, 1463, 1441, 1432, 1422, 1413, 1378, 1360, 1331, 1314, 1284, 1262, 1250, 1147, 1118, 1064, 1054, 1037, 1025, 989, 970, 913, 717, 678 and 658 cm$^{-1}$.

EXAMPLE 15

3-(5-[(1,1-dimethylethyl)dimethylsiloxy]hept-1-yl)cyclopentene
{[[5-(2-cyclopenten-1-yl)-1-ethylpentyl]oxy]1,1-dimethylethyl)dimethylsilane}

The procedure followed is the same as that described in Example 7 and 8 using 3-(5-hydroxyhept-1-yl)cyclopentene {alpha-ethyl-2-cyclopenten-1-pentanol} (32.5 g, 0.177 moles), t-butyldimethylsilylchloride (29.3 g, 0.194 moles), imidazole (13.3 g, 0.194 moles), and dimethylformamide (163 ml). The crude product is fractionally distilled under reduced pressure leaving a clear, colorless oil (48 g, 0.162 moles), BP 103° C./0.15 mm.

Analysis IR: 3046, 2925, 2850, 1460, 1445, 1404, 1374, 1358, 1252, 1214, 1183, 1127, 1108, 1064, 1055, 1005, 936, 909, 893, 857, 833, 812, 789, 771, 714, and 658 cm$^{-1}$.

EXAMPLE 16

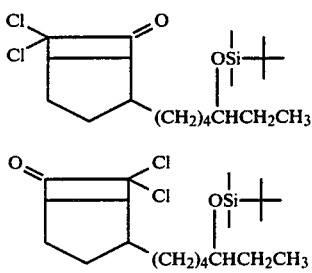

Alpha and beta isomers of
6,6-dichloro-2-(5-[(1,1-dimethylethyl)
dimethylsiloxy]hept-1-yl)bicyclo[3.2.0]heptan-7-one
{7,7-dichloro-4-[5-[[(1,1-dimethylethyl)dimethylsilyl-
]oxy]bicyclo [3.2.0]heptan-6-one]} and
7,7-dichloro-2-(5-[(1,1-dimethylethyl)
dimethylsiloxy]hept-1-yl)bicyclo[3.2.0]heptan-6-one
{7,7-dichloro-2-[5-[[(1,1-dimethylethyl)dimethylsilyl-
]oxy]bicyclo[3.2.0]heptan-6-one]}

The procedure followed is the same as that described in Example 9 substituting 3-(5-[(1,1-dimethylethyl)-dimethylsiloxy]hept-1-yl)cyclopentene {[[5-(2-cyclopenten-1-yl)-1-ethylpentyl]oxy]1,1-dimethylethyl)dimethylsilane} (0.162 moles, 48.0 g), trichloroacetyl chloride (0.324 moles, 59 g, 36.2 ml) phosphorous oxychloride (0.324 moles, 50 g, 30.2 ml). The crude product is kugelrohred and fractionally distilled under reduced pressure leaving a clear, colorless oil (36 g, 0.088 moles), BP 168° C./0.3 mm.

Analysis: IR: 2827, 2876, 2852, 1802, 1460, 1405, 1376, 1359, 1306, 1252, 1223, 1182, 1158, 1129, 1109, 1066, 1029, 1012, 966, 936, 896, 859, 833, 789, 771, 740, 672, 622, and 619 cm$^{31}$ $^1$.

EXAMPLE 17

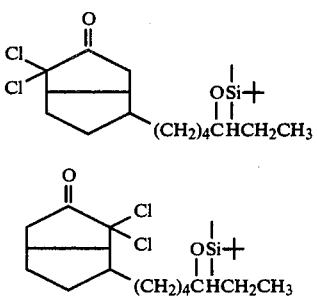

Alpha and beta isomers of
6,6-dichloro-2-(5-[(1,1-dimethylethyl)dimethylsiloxy]-
hept-1-yl)bicyclo[3.3.0]octan-7-one
{1,1-dichloro-4-[5-[[(1,1-dimethylethyl)dimethylsilyl-
]oxy]heptyl]hexahydro-2(1H)-pentalenone} and
8,8-dichloro-2-(5-[(1,1-dimethylethyl)dimethylsilox-
yhept-1-yl)bicyclo[3.3.0]octan-7-one
{1,1-dichloro-6[5-[[(1,1-dimethylethyl)dimethylsilyl-
]oxy]heptyl]hexahydro-2(1H)-pentalenone}

The procedure followed is the same as that described in Example 10 substituting the starting material from Example 16, 6,6-dichloro-2-(5-[1,1-dimethylethyl)dimethylsiloxy]hept-1-yl)bicyclo[3.2.0]heptan-7-one {7,7-dichloro-4-[5-[[(1,1-dimethylethyl)dimethylsilyl]oxy]- bicyclo[3.2.0]heptan-6-one]} and isomers (31.3 g, 0.093 moles). The crude product is chromatographed on silica gel leaving a clear yellow oil (9.7 g, 0.027 moles).

Analysis: IR: 2948, 2929, 2855, 1765, 1461, 1401, 1377, 1254, 1140, 1117, 1051, 1037, 1002, 965, 915, 891, 834, 772, 757, 726 and 709 cm$^{-1}$.

EXAMPLE 18

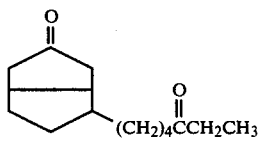

Alpha and beta isomers of
2-(5-oxohept-1-yl)bicyclo[3.3.0]octan7-one
{(hexahydro-4-(5-oxoheptyl))-2(1H)-pentalenone}

The procedure followed is the same as that described in Example 13 substituting the starting material from Example 3, 2-(5-hydroxyhept-1-yl)bicyclo[3.3.0]octan-7-one {hexahydro-4-(5-hydroxyheptyl)-2(1H)-pentalenone} (2.0 g, 8.4 mmoles) and pyridinium dichromate (4.7 g, 12.6 mmoles) in methylene chloride (10 ml). The crude product is chromatographed on silica gel and subsequently kugelrohred under vacuum leaving a clear, colorless oil (1.7 g, 7.1 mmoles).

Analysis: IR: 2939, 2860, 1740, 1714, 1461, 1451, 1406, 1376, 1243, 1209, 1161, and 1112 cm$^{-1}$.

Alpha and beta isomers of
6,6-dichloro-2-(5-oxohept-1-yl)bicyclo[3.2.0]heptan-
7-one
{7,7-dichloro-4-(5-oxoheptyl)bicyclo[3.2.0]heptan-6-
one} and
7,7-dichloro-2-(5-oxohept-1-yl)bicyclo[3.2.0]heptan-
6-one
{7,7-dichloro-2-(5-oxoheptyl)bicyclo[3.2.0]heptan-6-
one}

The procedure followed is the same described above substituting: 6,6-dichloro-2-(5-hydroxyhept-1-yl)bicyclo[3.2.0]heptan-7-one {7,7-dichloro-4-(5-hydroxyheptyl)bicyclo[3.2.0]heptan-6-one} and isomers (2.5 g, 8.6 mmoles), methylene chloride (18 ml), and pyridinium dichromate (6.4 g, 17.1 mmoles).

Analysis: IR: 2939, 2871, 1713, 1462, 1450, 1415, 1375, 1225, 1162, 1130, 1027, 966, 952, 811, 805, 730 and 672 cm$^{-1}$.

EXAMPLE 19

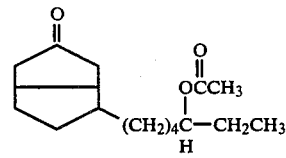

Alpha and beta isomers of
2-(5-acetoxyhept-1-yl)bicyclo[3.3.0]octan-7-one
{4-[5-(acetyloxy)heptyl]hexahydro-2(1H)-pentalenone}

The starting material from Example 3, 2-(5-hydroxyhept-1-yl)bicyclo[3.3.0]octan-7-one {hexahydro-4-(5-hydroxyheptyl)-2(1H)-pentalenone} (2.5 g, 10.5 mmoles) is diluted with glacial acetic acid (10 ml) and stirred in a 70° C. water bath for 4 hours. The reaction is cooled to room temperature and partitioned between ether (50 ml) and water (50 ml). The ether layer is separated and the aqueous phase extracted with ether (2×50 ml). The organic layers are combined, neutralized with a solution of saturated sodium bicarbonate, and dried over anhydrous sodium sulfate. The solvent is removed under vacuum leaving a clear yellow oil. The crude product is chromatographed on silica gel and subsequently kugelrohred under vacuum leaving a clear, colorless oil (2.1 g, 7.4 mmoles).

Analysis: IR: 2930, 2855, 1738, 1460, 1403, 1371, 1245, 1160, 1117, 1019 and 958 cm$^{-1}$.

EXAMPLE 20

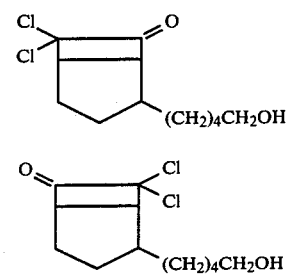

Alpha and beta isomers of
6,6-dichloro-2-(5-hydroxypent-1-yl)bicyclo[3.2.0]heptan-7-one
{7,7-dichloro-4-(5-hydroxypentyl)bicyclo[3.2.0]heptan-6-one} and
7,7-dichloro-2-(5-hydroxypent-1yl)bicyclo[3.2.0]heptan-6-one
{7,7-dichloro-2-(5-hydroxypentyl)bicyclo[3.2.0]heptan-6-one}

The procedure followed is the same as that described in Example 12 substituting the starting material from Example 9, 6,6-dichloro-2-(5-[(1,1-dimethylethyl)dimethylsiloxy]pent-1-yl)bicyclo[3.2.0]heptan-7-one {7,7-dichloro-4-[5-[[(1,1-dimethylethyl)dimethylsilyl]oxy]-pentyl]bicyclo[3.2.0]heptan-6-one} and isomers (32.1 g, 0.084 moles), hydrofluoric acid (8.0 ml), and acetonitrile (161 ml). The crude product is chromatographed on silica gel and subsequently kugelrohred under vacuum leaving a clear, colorless oil (20.1 g, 0.076 moles).

Analysis: IR: 3406 (broad), 2931, 2856, 1801, 1460, 1372, 1348, 1334, 1318, 1302, 1276, 1223, 1159, 1131, 1073, 1055, 1028, 992, 987, 970, 959, 915, 817, 739, and 623 cm$^{-1}$.

EXAMPLE 21

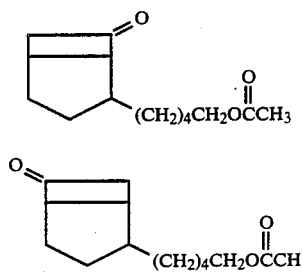

Alpha and beta isomers of
2-(5-acetoxypent-1-yl)bicyclo[3.2.0]heptan-7-one
{4-[5-(acetyloxy)pentyl]bicyclo[3.2.0]heptan-6-one}
and 2-(5-acetoxypent-1-yl)bicyclo[3.2.0]heptan-6-one
{2-[5-(acetyloxy)pentyl]bicyclo[3.2.0]heptan-6-one}

The starting material from Example 20, 6,6-dichloro-2-(5-hydroxypent-1-yl)bicyclo[3.2.0]heptan-7-one {7,7-dichloro-4-(5-hydroxypentyl)bicyclo[3.2.0]heptan-6-one} and isomers (7 g, 26 mmoles) is dissolved in glacial acetic acid (49 ml) and zinc powder (14 g) is added. The reaction is then heated in a 70° C. water bath and stirred for 4 hours. The reaction is cooled to room temperature and partitioned between ether (250 ml) and water (250 ml). The aqueous phase is extracted with ether (2×200 ml), the extracts are combined and then neutralized with a solution of saturated bicarbonate. The ether layer is dried over anhydrous sodium sulfate and the solvent removed under vacuum leaving a clear, colorless oil. The crude product is chromatographed on silica gel and subsequently kugelrohred under vacuum leaving a clear, colorless oil (2.0 g, 7.1 mmoles).

Analysis: IR: 2934, 2857, 1778, 1737, 1462, 1387, 1365, 1297, 1239, 1138, 1117, 1089, 1042, 973, and 705 cm$^{-1}$.

EXAMPLE 22

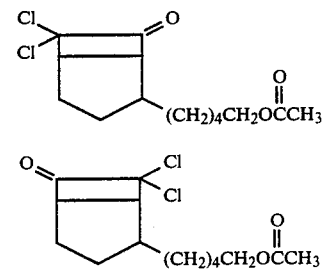

Alpha and beta isomers of
6,6-dichloro-2-(5-acetoxypent-1-yl)bicyclo[3.2.0]heptan-7-one
{4-[5-(acetyloxy)pentyl]-7,7-dichlorobicyclo[3.2.0]heptan-6-one} and
7,7-dichloro-2-(5-acetoxypent-1-yl)bicyclo[3.2.0]heptan-6-one
{2-[(5-acetyloxy)pentyl]-7,7-dichlorobicyclo[3.2.0]heptan-6-one}

The procedure followed is the same as that described in Example 19 substituting: the starting material from Example 20, 6,6-dichloro-2-(5-hydroxypent-1-yl)bicyclo[3.2.0]heptan-7-one {7,7-dichloro-4-(5-hydroxypentyl)bicyclo[3.2.0]heptan-6-one} and isomers (5 g, 19 mmoles) and glacial acetic acid (10 ml). The crude product is chromatographed on silica gel and subsequently kugelrohred under vacuum leaving a clear, colorless oil (4.1 g, 0.013 moles).

Analysis: IR: 2935, 2858, 1803, 1737, 1461, 1387, 1365, 1239, 1070, 1037, 817, 739, and 673 cm$^{-1}$.

EXAMPLE 23

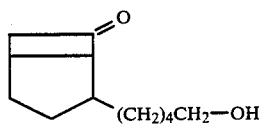

-continued

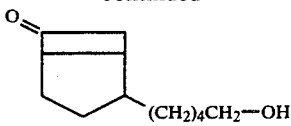

Alpha and beta isomers of
2-(5-hydroxypent-1-yl)bicyclo[3.2.0]heptan-6-one
{4-(5-hydroxypentyl)bicyclo]3.2.0]heptan-6-one} and
2-(5-hydroxypent-1-yl)bicyclo[3.2.0]heptan-7-one
{2-(5-hydroxypentyl)bicyclo[3.2.0]heptan-6-one}

The procedure followed is the same as that described in Example 3 substituting: the starting material in Example 20, 6,6-dichloro-2-(5-hydroxypent-1-yl)bicyclo[3.2.0]heptan-7-one {7,7-dichloro-4-(5-hydroxypentyl)bicyclo[3.2.0]heptan-6-one} and isomers (15 g, 0.057 moles), glacial acetic acid (105 ml), and zinc powder (30 g, 0.46 moles). The crude product is chromatographed on silica gel and subsequently kugelrohred under vacuum leaving a clear, colorless oil (4 g, 0.023 moles).

Analysis: IR: 3415 (broad), 2931, 2858, 1461, 1400, 1387, 1365, 1160, 1072 and 1044 cm$^{-1}$.

EXAMPLE 24

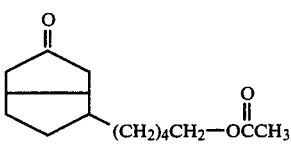

Alpha and beta isomers of
2-(5-acetoxypent-1-yl)bicyclo[3.3.0]octan-7-one
{4-[5-(acetyloxy)pentyl]hexahydro-2(1H)-pentalenone}

The starting material 2-(5-hydroxypent-1-yl)bicyclo[3.3.0]octan-7-one {hexahydro-4-(5-hydroxypentyl)-2(1H)-pentalenone} (0.8 g, 3.8 mmoles) is diluted with glacial acetic acid (7 ml). The reaction is stirred and heated in a 75° C. oil bath for 24 hours, after which time water (20 ml) is added and the reaction partitioned between ether. The ether layer is separated and the aqueous phase extracted again with ether (2×50 ml). The extracts and the organic phase are combined and neutralized with saturated sodium bicarbonate. The organic phase is dried over anhydrous magnesium sulfate and the remained solvent removed under vacuum leaving a pale yellow oil. The product is kugelrohred under reduced pressure leaving a clear, colorless oil (0.5 g, 2.0 mmoles).

Analysis: IR: 2932, 2856, 1739, 1462, 1404, 1385, 1365, 1239, 1160 and 1044 cm$^{-1}$.

EXAMPLE 25

5-Chloropentan-3-ol {1-chloro-3-pentanol}

The procedure followed is the same as that used in Example 6 substituting: 5-chloropentan-3-one {1-chloro-3-pentanone} (100 g, 0.83 moles) is dissolved in 95% ethanol (100 ml) and sodium borohydride (8.6 g, 0.23 moles) dissolved in 95% ethanol (200 ml). The crude product is fractionally distilled under reduced pressure leaving a clear, colorless oil (50 g, 0.41 moles), BP 40° C./1.4 mm.

Analysis: IR: 3348 (broad), 2969, 2934, 2874, 1462, 1454, 1446, 1413, 1377, 1344, 1309, 1299, 1210, 1172, 1128, 1094, 1079, 1060, 1051, 1022, 1013, 997, 980, 951, 862, 721, and 649 cm$^{-1}$.

EXAMPLE 26

(5-Chloro-3-pentyloxy)(2,2-dimethylethyl)dimethylsilane
{3-chloro-1-ethylpropoxy)(1,1-dimethylethyl)dimethylsilane}

The procedure followed is the same as that described in Example 7 substituting 5-chloropentan-3-ol {1-chloro-3-pentanol} (50 g, 0.41 moles), tert-butyldimethylsilyl chloride (71g, 0.47 moles), imidazole (32.6 g, 0.48 moles), and dimethylformamide (150 ml). The crude product is fractionally distilled under vacuum leaving a clear, colorless oil (78 g, 0.33 moles), BP 48° C./0.1 mm.

Analysis: IR: 2958, 2933, 2892, 2887, 2859, 2826, 2803, 1472, 1463, 1447, 1468, 1389, 1374, 1361, 1337, 1310, 1293, 1280, 1257, 1212, 1185, 1175, 1168, 1135, 1088, 1043, 1032, 1006, 958, 939, 913, 901, 837, 809, 775, 730, 712, 676, and 654 cm$^{-1}$.

EXAMPLE 27

3-(3-[(1,1-Dimethylethyl)dimethylsiloxy]pent-1-yl)cyclopentene
{[3-(2-cyclopenten-1-yl)-1-ethylpropoxy](1,1-dimethylethyl)dimethylsilane}

The procedure followed is the same as that described in Example 8 substituting (5-chloro-3-pentyloxy)(2,2-dimethylethyl)dimethylsilane {3-chloro-1-ethylpropoxy)(1,1-dimethylethyl)dimethylsilane} (78 g, 0.33 moles) diluted in tetrahydrofuran (100 ml), granular magnesium (24 g, 1.00 moles), tetrahydrofuran (100 ml), 0.1M solution of Li$_2$CuCl$_4$ (1.0 mmole), and 3-chlorocyclopentene (33 g, 0.33 moles) dissolved in tetrahydrofuran (50 ml). The crude product is distilled under reduced pressure leaving a clear yellow oil (21 g, 0.078 moles), BP 69° C./0.1 mm.

Analysis: IR: 3055, 2956, 2933, 2902, 2858, 1472, 1463, 1374, 1361, 1256, 1136, 1097, 1060, 1035, 1006, 835, 806, 774, 717, and 661 cm$^{-1}$.

EXAMPLE 28

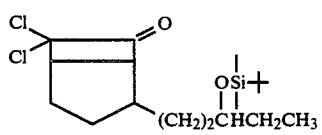

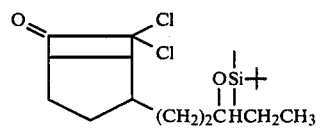

Alpha and beta isomers of
6,6-dichloro-2-(3-[(1,1-dimethylethyl)dimethylsiloxy]-
pent-1-yl)bicyclo[3.2.0]heptan-7-one
{7,7-dichloro-4-[3-[[(1,1-dimethylethyl)dimethylsilyl-
]oxy]pentyl]bicyclo[3.2.0]heptan-6-one} and
7,7-dichloro-2-(3-[(1,1-dimethylethyl)dimethylsiloxy]-
pent-1-yl)bicyclo[3.2.0]heptan-6-one
{7,7-dichloro-2-[3-[[(1,1-dimethylethyl)dimethylsilyl-
]oxy]pentyl]bicyclo3.2.0]heptan-6-one{

The procedure followed is the same as that described in Example 9 substituting: 3-(3-[(1,1-dimethylethyl)-dimethylsiloxy]pent-1-yl)cyclopentene {[3-(2-cyclopenten-1-yl)-1-ethylpropoxy](1, 1-dimethylethyl)dimethylsilane} (15 g, 0.056 moles) dissolved ether (100 ml), trichloroacetyl chloride (20.3 g, 0.11 moles) and phosphorous oxychloride (17.2 g, 0.11 moles) both dissolved in ether (50 ml), zinc/copper couple (10 g, 0.16 moles). The crude product is kugelrohred under vacuum leaving a clear yellow oil (13.5 g, 0.035 moles).

Analysis: IR: 2958, 2932, 2903, 2858, 1806, 1471, 1463, 1449, 1374, 1361, 1256, 1184, 1135, 1099, 1065, 1052, 1031, 1006, 669, 960, 939, 898, 835, 808, 774, 740, and 674 cm$^{-1}$.

EXAMPLE 29

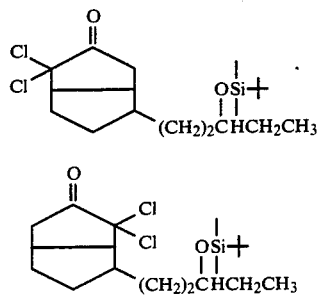

Alpha and beta isomers of
6,6-dichloro-2-(3-[(1,1-dimethylethyl)dimethylsiloxy]-
pent-1-yl)bicyclo[3.3.0]octan-7-one
{1,1-dichloro-4-[3-[[(1,1-dimethylethyl)dimethylsilyl-
]oxy]pentyl]hexahydro-2(1H)-pentalenone} and
8,8-dichloro-2-(3-[(1,1-dimethylethyl)dimethylsiloxy]-
pent-1-yl)bicyclo[3.2.0]octan-7-one
{1,1-dichloro-6-[3[[(1,1-dimethylethyl)dimethylsilyl-
]oxy]pentyl]hexahydro-2(1H)-pentalenone}

Diazomethane is generated in situ from N-methyl-N-nitroso-p-toluenesulfonamide (60 g, 0.28 moles) according to the standard procedure using the macro diazald kit (Aldrich). The starting material in Example 28, 6,6-dichloro-2-(3-[(1,1-dimethylethyl)dimethylsiloxy]pent-1-yl)bicyclo[3.2.0]heptan-7-one {7,7-dichloro-4-[3-[[(1,1-dimethylethyl)dimethylsilyl]oxy]pentyl]bicyclo[3.2.0]heptan-6-one} and isomers (8.5 g, 0.023 moles) is treated with an etheral diazomethane solution (100 ml) followed by methanol (4 ml). After 50 minutes the excess diazomethane is neutralized with the addition of acetic acid (10 ml). The ether solution is neutralized with a solution of saturated bicarbonate and then dried over anhydrous sodium sulfate. The solvent is removed under vacuum leaving a clear yellow oil. The crude product is chromatographed on silica gel leaving a clear light yellow oil (3.3 g, 8.5 mmoles).

Analysis: IR: 2957, 2933, 2884, 2859, 1769, 1472, 1463, 1450, 1389, 1375, 1361, 1281, 1273, 1256, 1186, 1136, 1097, 1080, 1051, 1005, 961, 939, 929, 891, 836, 808, 774, 744, 711, 675, and 661 cm$^{-1}$.

EXAMPLE 30

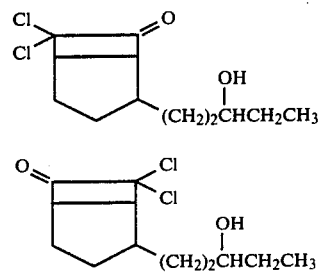

Alpha and beta isomers of
6,6-dichloro-2-(3-hydroxypent-1-yl)bicyclo[3.2.0]heptan-7-one
{7,7-dichloro-4-(3-hydroxypentyl)bicyclo[3.2.0]heptan-6-one} and
7,7-dichloro-2-(3-hydroxypent-1-yl)bicyclo[3.2.0]heptan-6-one
{7,7-dichloro-2-(3-hydroxypentvl)bicyclo[3.2.0]heptan-6-one}

The procedure followed is the same as that described in Example 12 substituting the starting material prepared in Example 28, 6,6-dichloro-2-(3-[(1,1-dimethylethyl)dimethylsiloxy]pent-1-yl)bicyclo[3.2.0]heptan-7-one {7,7-dichloro-4-[3-[[(1,1dimethylethyl)dimethylsilyl]oxy]pentyl]bicyclo[3.2.0]heptan-6one} and isomers (0.9 g, 2.4 mmoles), acetonitrile (20 ml), and hydrofluoric acid (1 ml). The crude product is chromatographed on silica gel and subsequently kugelrohred under vacuum leaving a clear colorless oil (0.55 g, 2.0 mmoles).

Analysis: IR: 3411 (broad), 2964, 2940, 2870, 1803, 1462, 1450, 1376, 1334, 1301, 1287, 1225, 1159, 1125, 1106, 1097, 1062, 1030, 1006, 1002, 964, 948, 938, 914, 871, 830, 818, 790, 743, and 675 cm$^{-1}$.

EXAMPLE 31

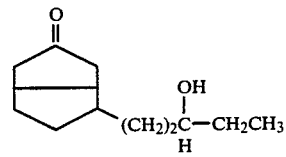

Alpha and beta isomers of
2-(3-hydroxypent-1-yl)bicyclo[3.3.0]octan-7-one
{hexahydro-4-(3-hydroxypentyl)-2(1H)-pentalenone}

The procedure followed is the same as that described in Example 11 substituting the starting material prepared in Example 28, 6,6-dichloro-2-(3-[(1,1-dimethylethyl)dimethylsiloxy]pent-1-yl)bicyclo[3.2.0]heptan-7-one {7,7-dichloro-4-[3,[[(1,1-dimethylethyl)dimethylsilyl]oxy]pentyl]bicyclo[3.2.0]heptan-6-one} and isomers (2.4 g, 6.1 mmoles), glacial acetic acid (17 ml), and zinc powder (5 g). The crude product is chromatographed on silica gel and subsequently kugelrohred under vacuum leaving a clear, colorless oil (1.0 g, 4.8 mmoles).

Analysis: IR: 3411, 2961, 1739, 1451, 1406, 1364, 1258, 1162, 1115, 1110, 1071, 1063, 1115, 1096, 1037, 1027, 917, 864, 809, 798, 736, 702, 689, 681, and 657 cm$^{-1}$.

EXAMPLE 32

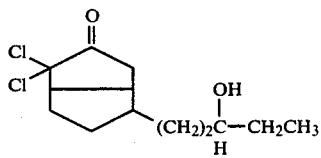

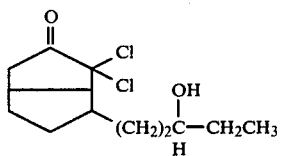

Alpha and beta isomers of 6,6-dichloro-2-(5-hydroxypent-1-yl)bicyclo[3.3.0]octan-7-one {1,1-dichlorohexahydro-4-(5-hydroxypentyl)-2(1H)-pentalenone} and 8,8-dichloro-2-(5-hydroxypent-1-yl bicyclo[3.3.0]octan-7-one {1,1-dichlorohexahydro-6-(5-hydroxypentyl)-2(1H)-pentalenone}

The procedure followed is the same as described in Example 12 substituting the starting material from prepared in Example 10, 6,6-dichloro-2-(5-[(1,1-dimethylethyl)dimethylsiloxy]pent-1yl)bicyclo[3.3.0]octan-7-one {1,1-dichloro-4-[5-[[(1,1-dimethylethyl)dimethylsilyl]oxy]pentyl]hexahydro-2(1H)-pentalenone} (2.0 g, 5.1 mmoles), acetonitrile (20 ml), and hydrofluoric acid (1.0 ml). The crude product is chromatographed on silica gel leaving a clear light yellow oil (1.2 g, 4.2 mmoles).

Analysis: IR: 3337 (broad), 2932, 2856, 1764, 1460, 1406, 1381, 1321, 891, 835, 818, 780, 763, 676, and 663 cm$^{-1}$.

EXAMPLE 33

3-(Hept-1-yl)cyclopentene {3-heptylcyclopenten}

The procedure followed is the same as that described in Example 8 substituting the starting material, 1-bromoheptane (100 g, 0.56 moles) dissolved in tetrahydrofuran (100 ml), granular magnesium (25 g) in tetrahydrofuran (100 ml), 0.1M solution of Li$_2$CuCl$_4$ (1.7 mmoles), and 3-chlorocyclopentene (57 g, 0.56 moles) dissolved in tetrahydrofuran (200 ml). The crude product is fractionally distilled under vacuum leaving a clear, colorless oil (49 g, 0.29 moles), BP 41° C./0.35 mm.

Analysis: IR: 3047, 2847, 2939, 2922, 2915, 2900, 2849, 1461, 1375, 1357, 1300, 1203, 1101, 1058, 975, 932, 910, 760, and 715 cm$^{-1}$.

EXAMPLE 34

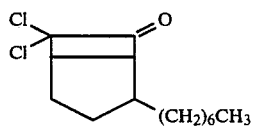

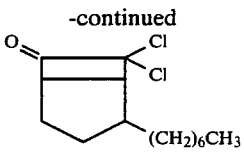

Alpha and beta isomers of 6,6-dichloro-2-(hept-1-yl)bicyclo[3.2.0]heptan-7-one {7,7-dichloro-4-heptylbicyclo[3.2.0]heptan- 6-one} and 7,7-dichloro-2-(hept-1-yl)bicyclo[3.2.0]heptan-6-one {7,7-dichloro-2-heptylbicyclo[3.2.0]heptan-6-one}

The procedure followed is the same as that described in Example 9 substituting the starting material prepared in Example 33, 3-(hept-1-yl)cyclopentene {3-heptylcyclopentene} (49 g, 0.30 moles) diluted in ether (490 ml), trichloroacetyl chloride (97 g, 0.53 moles) and phosphorous oxychloride (81 g, 0.53 moles) both diluted with ether (150 ml), zinc/copper couple (30 g, 0.59 moles) were used. The crude product is kugelrohred and subsequently fractionally distilled under reduced pressure leaving a clear, colorless oil (20.6 g, 0.075 moles), BP 115° C./0.22 mm.

Analysis: IR: 2955, 2925, 2853, 1803, 1464, 1451, 1380, 1225, 1030, 965, 815, 790, 740, 725, and 670 cm$^{-1}$.

EXAMPLE 35

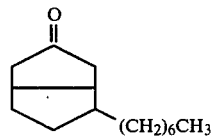

Alpha and beta isomers of 2-(hept-1-yl)bicyclo[3.3.0]octan-7-one {4-heptylhexahydro-2(1H)-pentalenone}

The procedure followed is the same as that described in Example 29 substituting the starting material from Example 34, 6,6-dichloro-2-(hept-1-yl)bicyclo[3.2.0-]heptan-7-one {7,7-dichloro-4-heptylbicyclo[3.2.0]heptan-6-one} and isomers (14.2 g, 0.051 moles), an etheral diazomethane solution (175 ml), methanol (5 ml), and acetic acid (15 ml). After the acetic acid is added the solvent is removed under vacuum leaving a clear yellow oil. The crude product is then dissolved in acetic acid (100 ml) and stirred while zinc powder (29 g) is slowly added. The reaction is heated in a 70° C. water bath for 1 hour, after which time ether (500 ml) is added and the solution filtered. The filtrate is washed with brine (100 ml) and then with a solution of saturated bicarbonate. The ether layer is separated and dried over anhydrous sodium sulfate. The solvent is removed under vacuum leaving a clear yellow oil. The crude product is chromatographed on silica gel and subsequently kugelrohred under vacuum leaving a clear, colorless oil (4.3 g, 0.015 moles).

Analysis: IR: 2949, 2922, 2852, 1740, 1465, 1404, 1375, 1239, and 1155 cm$^{-1}$.

EXAMPLE 36

Ethyl 5-ethoxyheptanoate

The starting material, a mixture of 5-hydroxyheptanoic acid and 6-ethyl-tetrahydro-2H-pyran-2-one (400 g) is added to a reaction vessel containing ethanol (4000 ml) and triethylorthoformate (4000 ml).

Perchloric acid (160 ml) is added slowly and the reaction is stirred at room temperature for 4 hours, after which time sodium hydroxide pellets (230 g) are added to stop the reaction. Once the perchloric acid has been neutralized the ethanol and triethylorthoformate are removed under vacuum. The residue is partitioned between ether (2000 ml) and water (1000 ml). The organic phase is separated and the aqueous layer extracted with ether (3×500 ml). The organic extracts are combined and dried over anhydrous sodium sulfate. The remaining solvent is removed under vacuum leaving a clear orange oil. The crude product is fractionally distilled under reduced pressure leaving a clear, colorless oil (302 g, 1.49 moles), BP 120° C./10 cm Hg.

Analysis: IR: 2971, 2933, 2874, 1736, 1461, 1448, 1418, 1400, 1372, 1348, 1300, 1241, 1196, 1177, 1106, 1076, 1035, 1014, 968, 921, 856, and 826 cm$^{-1}$.

EXAMPLE 37

5-Ethoxyheptanol

A solution of tetrahydrofuran (2000 ml) and lithium aluminum hydride (46 g, 1.21 moles) is cooled in a −60° C. dry ice/ethanol bath. The starting material prepared in Example 36, ethyl 5-ethoxyheptanoate (302 g, 1.49 moles) is diluted in tetrahydrofuran (300 ml) and added dropwise to the stirring reaction. After the addition is complete the reaction is warmed to room temperature and stirred for an additional hour. The solution is cooled in a −78° C. dry ice/ethanol bath and the excess hydride is destroyed by adding dropwise the following: water (46 ml), 15% sodium hydroxide solution (46 ml), and water (136 ml). The reaction is filtered and the solids washed several times with tetrahydrofuran (3×500 ml). The volume of the filtrate is reduced under vacuum and the residue dried over anhydrous magnesium sulfate. The remaining solvent is then removed leaving a clear, colorless oil suitably pure for the next reaction (238 g, 1.49 moles).

Analysis: IR: 3397 (broad), 2971, 2937, 2872, 1460, 1448, 1403, 1380, 1372, 1346, 1107, 1076, and 975 cm$^{-1}$.

EXAMPLE 38

1-Chloro-5-ethoxyheptane

The starting material prepared in Example 37, 5-ethoxyheptanol (238 g, 1.49 moles) is diluted in pyridine (128 g, 1.62 moles). The solution is stirred at room temperature and thionyl chloride (388 g, 3.22 moles) is added dropwise over 2 hours, after which time the reaction is heated in a 70° C. water bath for 2 additional hours. Water (700 ml) is added to the reaction and the organic layer separated. The aqueous layer is extracted with hexane (3×400 ml) and the extracts combined with the organic phase. The organic phase is then washed with a 10% sodium hydroxide solution (1000 ml). The solvent volume is reduced under vacuum and the residue dried over anhydrous magnesium sulfate. The remaining solvent is removed leaving a clear light yellow oil. The crude product is fractionally distilled under reduced pressure leaving a clear, colorless oil (162 g, 1.13 moles), BP 96° C./9.5 cm Hg.

Analysis: IR: 2968, 2933, 2868, 1459, 1445, 1400, 1370, 1344, 1309, 1157, 1107, 1076, 994, 979, 734, and 649 cm$^{-1}$.

EXAMPLE 39

3-(5-Ethoxyhept-1-yl)cyclopentene

The procedure followed is the same as that described in Example 8 with the following substitutions made: the starting material prepared in Example 38, 1-chloro-5-ethoxyheptane (162 g, 1.13 moles) dissolved in tetrahydrofuran (162 ml), granular magnesium (50 g, 2.1 moles) in tetrahydrofuran (500 ml), Li$_2$CuCl$_4$ (29.1 mmoles), and 3-chlorocyclopentene (89 g, 0.86 moles) diluted in 100 ml tetrahydrofuran was used. The crude product is distilled under reduced pressure leaving a clear, colorless oil (121 g, 0.575 moles), BP 76° C./0.34 mm.

Analysis: IR: 3049, 2967, 2928, 2852, 1460, 1443, 1369, 1343, 1154, 1110, 1081, 980, 715, and 678 cm$^{-1}$.

EXAMPLE 40

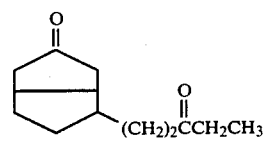

Alpha and beta isomers of 2-(3-oxopent-1-yl)bicyclo[3.3.0]octan-7-one {hexahydro-4-(3-oxopentyl)-2(1H)-pentalenone}

The procedure followed is the same as that described in Example 13, making the following substitutions made: the starting material prepared in Example 31, 2-(3-hydroxypent-1-yl)bicyclo[3.3.0]octan-3-one {hexahydro-4-(3-hydroxypentyl)-2(1H)-pentalenone} (0.8 g, 3.8 mmoles), and pyridinium dichromate (0.82 g, 2.1 mmoles) dissolved in methylene chloride (10 ml). The crude product is chromatographed on silica gel and subsequently kugelrohred under reduced pressure leaving a clear, colorless oil (0.55 g, 2.6 mmoles).

Analysis: IR: 2964, 1739, 1714, 1450, 1403, 1364, 1255, 1168, 1115, 1110, 1063, 915, and 864 cm$^{-1}$.

EXAMPLE 41

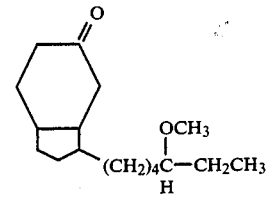

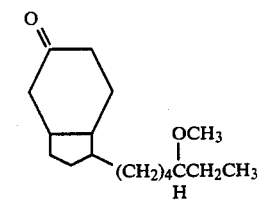

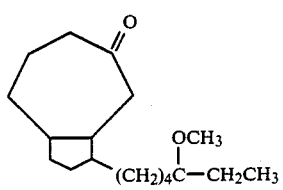

-continued

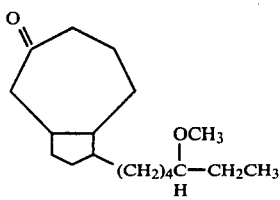

Alpha and beta isomers of
9-(5-methoxyhept-1-yl)bicyclo[4.3.0]nonan-3-one
{octahydro-3-(5-methoxyheptyl)-5H-inden-5-one} and isomer
7-(5-methoxyhept-1-yl)bicyclo[4.3.0]nonan-3-one{octahydro-1-(5-methoxyheptyl)-5H-inden-5-one} and
8-(5-methoxyhept-1-yl)bicyclo[5.3.0]decan-3-one
{octahydro-3-(5-methoxyheptyl)-5(1H)-azulenone} and isomer
10-(5-methoxyhept-1-yl)bicyclo[5.3.0]decan-3-one
{octahydro-1-(5-methoxyheptyl)-5(1H)-azulenone}

Diazomethane is generated in situ from N-methyl-N-nitroso-p-toluenesulfonamide (60 g, 0.28 moles) according to the standard procedure using the macro diazald kit (Aldrich). The starting material in Example 4, 6,6-dichloro-2-(5-methoxyhept-1-yl)bicyclo[3.2.0]heptan-7-one {7,7-dichloro-4-(5-methoxyheptyl)bicyclo[3.2.0]heptan-6-one} and isomers (8 g, 0.026 moles ) is treated with an etheral diazomethane solution (100 ml) followed by methanol (4 ml). After 50 minutes the excess diazomethane is neutralized with the addition of acetic acid (10 ml). The solvent is removed under vacuum leaving a clear yellow liquid. The crude product is then diluted with acetic acid (240 ml) and stirred while zinc powder (72 g, 1.10 moles) is slowly added. The reaction is heated in a 70° C. water bath for 1 hour, after which time ether (500 ml) is added and the solution filtered. The ether layer is washed with brine (100 ml) and then with a solution of saturated bicarbonate. The ether layer is separated and dried over anhydrous sodium sulfate. The solvent is removed under vacuum leaving a clear yellow oil. The crude product is chromatographed on silica gel. The two desired products are isolated. The first product is comprised of 9-(5-methoxyhept-1-yl)bicyclo[4.3.0]nonan-3-one {octahydro-3-(5-methoxyheptyl)-5H-inden-5-one} and 7-(5-methoxyhept-1-yl)bicyclo[4.3.0]nonan-3-one {octahydro-1-(5-methoxyheptyl)-5H-inden-5-one} (1.2 g, 4.5 mmoles) and the second product mainly 8-(5-methoxyhept-1-yl)bicyclo[5.3.0]decan-3-one {octahydro-3-(5-methoxyheptyl)-5(1H)azulenone} and isomer 10-(5-methoxyhept-1-yl)bicyclo[5.3.0]decan-3-one {octahydro-1-(5-methoxyheptyl)-5(1H)-azulenone} (0.3 g, 1.1 mmoles).

Product 1

Analysis: IR: 2932, 2850, 2817, 1730, 1460, 1400, 1379, 1366, 1155, 1130, 1093, 1050, 1037, 965, and 740 cm$^{-1}$.

Product 2

Analysis: IR: 2928, 2850, 2822, 1722, 1455, 1404, 1375, 1360, 1155, 1147, 1130, 1090, 1054, 1033, 955, 865, 740 cm$^-$.

EXAMPLE 42

Alpha and beta isomers of
2-(4-formylbutan-yl)bicyclo[3.3.0]octan-7-one
{octahydro-5-oxo-1-pentalenepentanal}

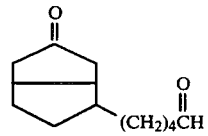

The procedure followed is the same as that described in Example 13 substituting the starting material prepared in Example 11, 2-(5-hydroxypent-1-yl)bicyclo[3.3.0]octan-7-one {hexahydro-4-(5-hydroxypentyl)-2(1H)-pentalenone} (0.3 g, 1.4 mmoles), and pyridinium dichromate (0.80 g, 2.1 mmoles) dissolved in methylene chloride (5 ml). The crude product is chromatographed on silica gel leaving a clear, colorless oil (0.14 g, 0.67 mmoles).

Analysis: IR: 2957, 2922, 2851, 2730, 1737, 1725, 1460, 1404, 1375, 1259, 1149, 1107, 1036, 1016, 792, 785, 658, 638 cm$^{-1}$.

Using the procedures described above, the following compounds were prepared and characterized by the spectral data given.

2-(5-Hydroxyheptylidene)bicyclo[3.3.0]octan-7-one

Analysis: IR: 3400, 2935, 2860, 1745, 1660, 1465, 1410, 1170, 1165, 1085, 1040, 935, 850, and 735 cm$^{-1}$.

The anti-androgenic activity of the compounds of the structure (I) can be demonstrated by essays like that of Thomas and Oake, "Androgen Metabolism in the Skin of Hirsute Women", J.C.E. and M., Vol. 38, page 19 (1974).

EXAMPLE 43

Compounds IV and V were tested to determine their percent inhibition of labelled androgen binding to the skin, the test utilizing caesarean section skin from hirsute patients:

| Ratio of Compound to Androgen Binding to Skin | % Inhibition of $^3$H Androgen | |
|---|---|---|
| | Compound IV | Compound V |
| 10:1 | 25% | 32% |
| 100:1 | 51% | 55% |
| 1000:1 | 75% | 80% |
| 10000:1 | 83% | 86% |

In skin samples from hirsute patients the compounds in this invention blocked the binding of $^3$H DHT to the androgen receptor site. DHT was selected for use in the assay because it is a more potent androgen than testosterone and exhibits a greater (stronger) affinity for the receptor site. Furthermore, there is evidence that 5 alpha reductase enzyme converts testosterone to DHT in vivo, and it is DHT which is the active steroid on the in vivo receptor sites.

In order to substantiate the effects of the derived anti-androgen compounds on actual balded scalp specimens, skin was obtained from volunteers undergoing hair transplantation. The bald skin was used for androgen receptors using the second technique described above. The androgen used was dihydrotestosterone (DHT) vs. the anti-androgen compounds afore herein recited.

The results with compounds IV and V are shown on following table:

| % Inhibition of Binding ³H DHT to Androgen Receptor COMPOUND IV | | | | | |
|---|---|---|---|---|---|
| PATIENT # | 10:1 | 20:1 | 100:1 | 200:1 | 1000:1 |
| | Ratio of Compound IV: ³H DHT | | | | |
| #1 | 25% | 30% | 35% | 39% | 42% |
| #2 | 40% | 47% | 69% | 72% | 75% |
| #3 | 0% | 0% | 13% | 15% | 22% |
| #4 | 14% | 43% | 45% | 47% | 50% |
| #5 | 17% | 46% | 46% | 48% | 50% |
| #6 | 15% | 36% | 37% | 39% | 43% |
| | Ratio of Compound V: ³H DHT | | | | |
| #1 | 50% | 60% | 67% | 68% | 70% |
| #2 | 43% | 59% | 74% | 76% | 77% |
| #3 | 0% | 0% | 17% | 18% | 25% |
| #4 | 19% | 47% | 47% | 48% | 50% |
| #5 | 23% | 51% | 51% | 52% | 54% |
| #6 | 18% | 41% | 42% | 45% | 50% |

Again, the nonhirsute patient (having less androgenic sites available for interaction) displayed the preferred uptake for the natural androgen over any of the new family of anti-androgens. This data supports the concept of a higher $K_d$ for these anti-androgen compounds compared with that of the natural androgen:

| % Inhibition of Binding 3H DHT to Androgen Receptor Ratio of Compound to ³H DHT | | | | |
|---|---|---|---|---|
| Compound | 10:1 | 100:1 | 1,000:1 | 10,000:1 |
| IV | 52 | 60 | 64 | 68 |
| V | 40 | 47 | 56 | 65 |

Competitive inhibition experiments were performed using compound IV in the second technique described above. The results are presented in the following tables.

As noted below, the test compound inhibited the androgen receptor site at 10 molecules of compound IV or of compound V for one molecule of testosterone. The degree of inhibition increased as the ratio of compound/androgen increased.

The in vitro interaction of compounds IV and V with dihydrotestosterone are recorded below.

The ratio of 10 or 20 to 1 is readily exceeded by topical therapy, as the ratio of compound IV to androgen applied topically in the small therapeutic trial was in excess of 10,000 to 1. This lipophilic molecule would be concentrated in the pilosebaceous glands. In vitro inhibition of the andrgen receptor-DHT interaction by Compound IV and Compound V.

| Ratio of Compound Androgen to Androgen | Femtamoles of DHT Bound/mg Protein* | % of Receptor Inhibition |
|---|---|---|
| Compound IV | | |
| 0:1 | 78 | 0 |
| 10:1 | 58 | 25.6 |
| 100:1 | 46 | 41.0 |
| Compound V | | |
| 0:1 | 78 | 0 |
| 10:1 | 44 | 43.6 |
| 100:1 | 38 | 51.3 |

*Corrected for non-specific binding

In vitro inhibition of the Androgen receptor-testosterone interaction by Compound IV and Compound V.

| Ratio of Compound to Androgen | Femtamoles of Testosterone Bound/mg Protein* | % of Androgen Receptor Inhibition |
|---|---|---|
| Compound IV | | |
| 0:1 | 3.6 | 0 |
| 20:1 | 2.0 | 43.7 |
| Compound V | | |
| 0:1 | 3.6 | 0 |
| 20:1 | 1.9 | 47.0 |

*Corrected for non-specific binding

EXAMPLE 44

Wrinkling of the skin involves the decreased formation of elastin and the increased formation of collagen by supporting cells, predominantly the fibroblasts. Experiments show that the control (non-treated) cells had only trace elastin production but copious collagen production. The cells treated with the compound IV, V and VI of formula produce a significant increase in elastin production on the order of 30% with a resultant decrease in collagen production.

EXAMPLE 45

Collagen formation has been found to be decreased in experiments with compounds of formulas IV, V and VI inclusive, whilst showing a massive observable increase in the formation of elastin. It is to be recognized that peripheral effects such as those on the arteries and dermis, do not alter the basic and hormonal essential functions of the androgens, and provides a beneficial result.

EXAMPLE 46

The following results were observed at concentrations of anti-androgen of formula V to DHT of 1,000:1

| Patient | % of Collagen Synthesized | Fold Elastic Increase Compared to Control |
|---|---|---|
| 1 | 23 | 1.4 |
| 2 | 23 | 4.7 |
| 3 | 54 | 2.0 |
| 4 | 43 | 4.0 |
| 5 | 59 | 6.0 |
| 6 | 63 | 2.0 |
| 7 | 39 | 3.0 |
| 8 | 41 | 3.0 |
| 9 | 66 | 4.0 |
| 10 | 57 | 6.0 |
| 11 | 39 | 3.0 |

These quantitative experiments demonstrate the importance of the anti-androgen and its therapeutic use in the topical application for altering collagen:elastin formation, thus decreasing wrinkles; but more importantly, its systemic applications would include its use in decreasing the rate of arteriosclerosis by decreasing the rate of collagen formation.

EXAMPLE 47

The compound of formula V was found to block 59–80% of androgen binding sites in a melanoma at concentrations of 1:1000 of dihydrotestosterone to the tested compound, with no significant effect on either the estrogen or progesterone receptors in the tissue.

EXAMPLE 48

Keloid formation is suppressed by blocking androgen receptor sites. In its generic aspect, the invention comprises a method of suppressing the formation of keloids which comprises topically applying to a patient an anti-androgenic agent to the skin of said patient, whereby androgen receptor sites are blocked, thereby retarding the formation of keloids. Tests conducted with 2-(5-methoxyhept-1-yl)bicyclo[3.3.0]octan-7-one {hexahydro-4-(5-methoxyheptyl)-2(1H)-pentalenone} have shown the suppression of keloid formation. Surgical excision of keloids was performed from clinic and private patient populations. 2-(5-Methoxyhept-1-yl)bicyclo[3.3.0]octan-7-one {hexahydro-4-(5-methoxyheptyl)-2(1H)-pentalenone} (Compound V) was incubated in ratios of 1 to 1:1,000 steroid hormone to this compound. Non-specific binding was determined with a 200-fold excess of unlabelled ligand at each concentration of $^3$H-ligand use. Male patients showed neither detectable estrogen or progesterone binding. The mean DHT binding was 867 femtamoles/mg cytosol-protein ±101 femtamoles/mg. The following results were obtained:

| Pt | Sex | Race | Age | Location of Keloid | Binding of DHT | % Block | Binding of Estrogen | Binding of Progesterone |
|---|---|---|---|---|---|---|---|---|
| 1 | F | Blk | 37 | Suprapubic | 703 | 43 | 9 | 7 |
| 2 | F | Blk | 21 | Chest | 816 | 24 | 4 | Non-detectable |
| 3 | M | Cauc | 23 | Neck | 795 | 57 | Non-detectable | Non-detectable |
| 4 | M | Blk | 26 | Inguinal groin | 938 | 86 | Non-detectable | Non-detectable |

Treatment for the prevention of interabdominal and other post surgical systemic adhesions were also evaluated. Skin fibroblast collagen suppression was also considered in using surgical explants.

At ratios of DHT: 2-(5-methoxyhept-1-yl)bicyclo[3.3.0]octan-7-one {hexahydro-4-(5-methoxyheptyl)-2(1H)-pentalenone} of 1:1,000, in more than 400 experiments, the 2-(5-methoxyhept-1-yl)bicyclo[3.3.0]octan-7-one {hexahydro-4-(5-methoxyheptyl)-2(1H)-pentalenone} blocked between 22% and 94% of the androgen receptors without significant interference with either the estrogen or progesterone receptors. Tissue taken from the keloid showed androgen receptor inhibition of 41 to 72% and no measurable estrogen or progesterone receptor inhibition. Scalp samples showed from 22 to 89% androgen inhibition and 0 to 7% progesterone inhibition. Forearm samples showed 22% androgen receptor inhibition and 4% progesterone receptor inhibition. None of the tests showed any measurable estrogen receptor inhibition.

"Hard fibrous band" formation was retarded around breast implants following augmentation surgery. Blockage of 34% to 79% of the androgen receptor sites was observed for the compound 2-(5-methoxyhept-1-yl)bicyclo[3.3.0]octan-7-one {hexahydro-4-(5-methoxyheptyl)-2(1H)-pentalenon} with no significant effects on either the estrogen or progesterone binding sites. The amount protein (in mg) per gram of gross tissue was measured for four breast capsule group numbers which showed:

| Mean % Androgen Binding | Mean % Androgen Inhibition |
|---|---|
| 10.7 | 17 |
| 31.0 | 49 |
| 99.9 | 70 |
| 109.8 | 74 |

The role of excessive androgen metabolism as a possible etiological factor in keloid formation has been reported. Briefly, the supportive evidence of this hypothesis is as follows:

(1) Keloids have a predilection to form on specific body sites such as the head, neck chest, upper back, inguinal and groin areas. These are the same areas that have been demonstrated to have high androgen metabolism.

(2) Keloid formation is frequently associated with other dermatological conditions such as acne vulgaris, acne conglobata, and hydradenitis superatasion. The diseases are thought to be caused by a localized excessive androgen metabolism.

(3) Keloids are rarely found in pre-pubescent children.

(4) The predisposition of keloid formation decreases after age 40.

(5) Keloids bind dihydrotestosterone in very high concentrations whereas the receptor levels for both estrogen and progesterone are very low.

The gamut of therapies for keloids has included x-ray irradiation, surgical excision, cryosurgery, as well as several other modalities, but the ideal therapy has not been found.

Because excessive androgen metabolism may be a factor in keloid growth, anti-androgens were investigated to test their efficacy on this problem.

EXAMPLE 49

Steroid Binding Assays

The specimens were prepared as in the preceding assays. However, in addition to assessing the binding activity of the keloid cytosols to the sex hormones, the novel anti-androgen was incubated in ratios of 1:0 to 1:1,000 steroid hormone to the anti-androgen. The non-specific binding was determined by adding a 200-fold excess of unlabelled ligand at each concentration of $^3$H-ligand use.

Chemicals

Tritiated steroids, 17-beta-estradiol [2,4,5,7-$^3$H] S.A. 90–100 ci/mmole, promegestone [17-alpha-methyl-$^3$H], S.A. 85–95 ci/mmole, and dihydrotestosterone [1,2,4,5,6,7-$^3$H] S.A. 130–140 ci/mmole and unlabelled steroids were obtained from New England Nuclear Corporation, Boston, Mass. Dextran T-70 was obtained from Pharmacia, Inc., New Jersey. All other chemicals were of reagent grade and obtained from commercial sources.

Results

The patient profile is recorded in Example 48. The male patients had neither detectable estrogen nor progesterone binding. Mean DHT binding occurred at 867 femtamoles/mg cytosol protein±101 femtamoles/mg.

Keloids have very high androgen binding and low to absent estrogen and progesterone binding activity. The supportive evidence suggests that androgen metabolism may be related to the formation of keloids. These experiments report the interaction of the anti-androgen of the invention with the sex hormone binding proteins for estrogen and progesterone and androgen. There was no effect on the binding of either estrogen or progesterone caused by the anti-androgen. However, the DHT binding was markedly altered by the anti-androgen in a competitive fashion. The degree of inhibition in the DHT binding varied from 43% to 75%. Of interest was the plateauing of the competitive blockage of DHT which occurred in ratios of nearly 100:1.

There are many possible explanations for this observation. A tenable explanation is that certain DHT binding sites are simply not blockable by the anti-androgen. The population of more readily blockable sites may represent excess binding proteins that are responsible for the excessive collagen formation that is characteristic of keloids. Conversely, the unblockable sites may be those which are responsible for the more essential functions which are mediated by DHT and have a higher affinity for the ligand than do the "excess sites. The plateau portions of the curve indicate that the anti-androgen, irrespective of its concentration, will not block all the DHT binding. The clinical implication is that the anti-androgen of the invention will not interfere with more essential androgen functions. Furthermore, an overdose of the anti-androgen during keloid therapy will not be possible. The anti-androgen had no effect on either the estrogen or progesterone binding activity, indicating that it acts selectively as an anti-androgen.

EXAMPLE 50

Treatment for Prevention of Interabdominal and Other Post Surgical Systemic Adhesions One of the hazards of surgery is adhesions. It is well known, and widely accepted that post operative adhesions are the most common and serious long term complications of surgery. Thus far there does not exist a satisfactory means to prevent the formation of intradominal adhesions in all operations. The most common method is addition of Dextran-70 intraabdominally following surgery. However, this often results in a decrease in homeostatis, the assumed mechanism of action in making peritoneal surfaces "slicker". Other mechanisms include the presence of blood, and drying, foreign material (Ryan et al., *American Journal of Pathology*, Vol. 65, pages 117–138 (1971)); Neuwrither and Khalal, S., *American Journal of Obstetrics and Gynecology*, Vol. 121, pages 42–411). However, these methods are not satisfactory. Other methods have included adding corticosteroids and proteolytic enzymes (Jarvimen, P. and Nummi, S., Acta *Obstetrics and Gynecology*, Vol. 55, page 281 (1976). In addition, the use of anti-inflammatory agents such as Ibuprofen (O'Brien et al., *Obstetrics and Gynecology*, Vol. 60, page 373 (1982)) in combination with steroids has also been attempted. However, this has also been unsatisfactory (Holtz, G., *Journal of Fertility and Sterility*, Vol. 37, page 582 (1982)). Because adhesions are fibroblastic cells elaborating collagen it was elected to obtain tissue fibroblasts from dense and filmy adhesions to assess the effect of different drugs in tissue cultures. These tissues were obtained from explants from dense adhesions from patients with both pre-operative irradiation, prior to surgical intervention, as well as patients without prior radiation. The amount of collagen was measured. It was found in the dense adhesions that there were higher numbers of androgen receptors in this group as compared to the very filmy adhesions. Thus, the major difference consisted of the number and density of fibroblastic androgen receptors. It was found that by incubation in vitro, the amount of fibroblast collagen synthesized by dense adhesions could be decreased to normal levels with the subject anti-androgen of this invention. Of marked interest was that the anti-androgen had less effect on the normal tissues (thus again, indicating the pathogenic nature of an over abundance of androgen receptors causing, or at least being a manifestation of abnormal collagen metabolism) and blocked the collagen production in these tissues in vitro.

In the female, adhesion formations following inflammatory pelvic disease is the most common cause of sterility. The septic abcess model that causes the adhesions was developed by Hunter A. Hammill et al. and was given at the Interscience Congress for Microbiology in Miami (October 1982). This model was used to assess the effects of the anti-androgen on the interperitoneal adhesions, as it is a model of human tubo-ovarian abcess (TOA) in the rat. The rats with TOA's were treated with antibiotics to cure the infection and the anti-androgen (100 mg) to decrease adhesions. It was found in double-blind control study that adhesion formation was markedly decreased in the subject anti-androgen treated group and not in the control group and thus the treatment of interabdominal adhesions can best be achieved by the anti-androgen alone or in combination.

EXAMPLE 51

Skin Fibroblast Collagen Suppression

Skin fibroblast tissue lines from surgical explants were obtained for studies with anti-androgen of the invention. Explants of both normal and keloid skin and tissue fibroblast lines were established.

Hormonal receptor analyses on these tissues were performed by the method of Griffith et al., *Journal of Clinical Investigation*, Vol. 57, page 1340 (1978). Such sensitive assays do not have SHBG interference and hence are the most exact measurements of receptor activity.

At ratios of DHT:anti-androgen of Compound V of 1:1,000, in more that 400 experiments, the subject anti-androgen blocked between 22%–94% of the androgen receptors without significant interference with either the estrogen or progesterone receptors.

| Tissue Culture No. | % Androgen Receptor Inhibition | % Estrogen Receptor Inhibition | % Progesterone Receptor Inhibition |
|---|---|---|---|
| Keloid | 72 | 0 | 0 |
| Keloid | 41 | 0 | 0 |
| Scalp | 22 | 0 | 7 |
| Scalp | 67 | 0 | 0 |
| Scalp | 89 | 0 | 3 |
| Forearm | 22 | 0 | 4 |

EXAMPLE 52

Prevention of "Hard Fibrous Band" Formation Around Breast Implants Following Breast Augmentation Surgery In addition to interabdominal adhesions following surgery, the other most common post-surgical fibrous complication is that of a hard fibrous band developing around breast implants following breast augmentation surgery. It has been postulated that these bands may be caused by keloid formation under the skin. Such tissues were studied to evaluate the effect of the anti-androgens of this invention on other keloid tissue.

After the evaluation of the subject hard band tissues it was found that the tissues contained a marked, and very high number, of androgen receptors. The tissues were evaluated, with appropriate controls, for effects by the novel anti-androgen.

The anti-androgen blocked 34%-79% of the androgen receptors without any significant effects on either estrogen or progesterone receptors.

As shown in the following summary table, the four groups were differentiated by the amount of protein (mg) per gram of gross tissue.

| Breast Capsule Group Number | Mean % Androgen Binding | Mean % Androgen Inhibition |
|---|---|---|
| 1 | 10.7 | 17 |
| 2 | 31.7 | 49 |
| 3 | 99.9 | 70 |
| 4 | 109.8 | 74 |

The test procedures set forth in Examples 50-52 may be repeated with the compound 2-(5-hydroxyhept-1-yl)bicyclo[3.3.0]octan-7-one {hexahydro-4-(5-hydroxyheptyl)-2(1H)-pentalenone}.

EXAMPLE 53

The compound 2-(5-methoxyhept-1-yl)bicyclo[3.3.0]octan-7-one {hexahydro-4-(5-methoxyheptyl)-2(1H)-pentalenone} was tested for its ability to block androgen receptor sites and has been found to produce excellent results in retarding collagen formation through blockage of androgen receptor sites. Accordingly, to treat arteriosclerosis, an oral dosage unit formulation is produced which contains 2 mg of 2-(5-methoxyhept-1-yl)bicyclo [3.3.0]octan-7-one {hexahydro-4-(5-methoxyheptyl)-2(1H)-pentalenone}, which is delivered to a subject once every six hours. Following the in vitro results, it is expected that collagen formation is retarded, thereby depriving the bloodstream of sites for formation of plaque, and thus alleviating the onset of arteriosclerosis.

The procedure of 53 is repeated with the compound 2-(5-hydroxyhept-1-yl)bicyclo[3.3.0]octan-7-one {hexahydro-4-(5-hydroxyhept-1-yl)bicyclo[3.3.0]octan-7-one {hexahydro-4-(5-hydroxyheptyl)-2 (1H)-pentalenone} and provides similar results. Experiments have demonstrated that this compound is an anti-androgenic compound operating in the same manner as the compound 2-(5-methoxyhept-1-yl)bicyclo[3.3.0]octan-7-one {hexahydro-4-(5-methoxyheptyl)-2(1H)-pentalenone} in similar in vitro tests.

Compounds of formula (I), especially Compounds IV, and V show valuable inhibitory effects on species of Fusarium, which produce damage to agriculture. It is also known that these fungi elaborate zearalenone and zearalanol which are toxic substances to livestock ingesting the grain rotted by them. Ingestion of these toxic substances is known to influence the prepubertal development of pigs (Berger et al., *Journal of Animal Science*, Vol. 53, pages 1559–1564 (1981). Zearalenone and zearalanol also affect milk production, breeding and pregnancy in such large livestock animals as pigs, cows and horses (Young et al., *Journal of Animal Science*, Vol. 54, pages 976–982). The Fusarium family of fungi also adversely affect chicken, turkey and other poultry animal populations (Allen et al., *Poultry Science*, Vol. 60, pages 124–131 (1981); Mirocha et al., *Poultry Science*, Vol. 60, pages 19–25 (1981)). Because of the importance of livestock production, the effect of the anti-androgens of this invention on these fungi was extensively studied. There is no currently available satisfactory treatment for the fungi nor the fungal hormones they elaborate (i.e., zearalenone and zearalanol).

The compound 2-(5-hydroxyhept-1-yl)bicyclo[3.3.0]octan-7-one {hexahydro-4-(5-hydroxyheptyl)-2(1H)-pentalenone} was observed to block 9-83% of the fungal androgen receptors at concentrations of DHT:compound of 1:1,000. The growth rate, colony counts and production of zearalenone and zearalanol are markedly decreased.

| Fungal Hormone | % Androgen Receptor Inhibition | % Estrogen Receptor Inhibition | % Progesterone Receptor Inhibition |
|---|---|---|---|
| Zeralenone | 79 | 0 | 0 |
| Zeralanol | 84 | 0 | 0 |

EXAMPLE 54

In the second series of experiments using the compound of the invention 2-(5-hydroxyhept-1-yl) bicyclo[3.3.0]octan-7-one {hexahydro-4-(5-hydroxyheptyl)-2-(1H)-pentalenone} upon zeralenone and zearalanol production, zearalenone and zearalanol were chemically obtained from Sigma Chemical Co., St. Louis, Mo. The subject compund was observed to directly interfere with the interaction of the fungal hormone and its hormonal receptors. Such blocking was observed to be from 26–90% at concentrations of the hormone: anti-androgen of 1:1 to 1:1,000

| Fungal Hormone | Ratio DHT:Anti-androgen | % Androgen Receptor Inhibition | % Estrogen Receptor Inhibition | % Progesterone Receptor Inhibition |
|---|---|---|---|---|
| Fusarium calorum | 1:1 | 29 | 0 | 7 |
|  | 1:10 | 37 | 0 | 9 |
|  | 1:100 | 79 | 0 | 6 |
|  | 1:1,000 | 90 | 0 | 4 |
| Fulsarium gravarium | 1:1 | 26 | 0 | 1 |
|  | 1:10 | 49 | 0 | 3 |
|  | 1:100 | 67 | 0 | 6 |

| Fungal Hormone | Ratio DHT:Anti-androgen | % Androgen Receptor Inhibition | % Estrogen Receptor Inhibition | % Progesterone Receptor Inhibition |
|---|---|---|---|---|
| | 1:1,000 | 87 | 0 | 4 |

EXAMPLE 55

Acceleration or Depression of the Fermentation Processes of Various Fungi

Brewers's yeast, Saccharomyces cerevisiae, is commonly used for fermentation in baking, liquor production and the alcohol production commercial industries.

Estrogen, progesterone and androgen receptors have been found in twelve strains of saccharomyces cerevisiae.

Subsequent thereto, 2-(5-hydroxyhept-1-yl)bicyclo[3.3.0]octan-7-one {hexahydro-4-(5-hydroxyheptyl)-2(1H)-pentalenone} was investigated, at a ratio of DHT:anti-androgen of 1:1,000, for its effects on the fermentation processes of these various strains of the fungus. The following table illustrates the findings.

| Saccharomyces Cervisiae Strain | % Androgen Receptor Inhibition | % Estrogen Receptor Inhibition | % Progesterone Receptor Inhibition |
|---|---|---|---|
| 1 | 16 | 0 | 2 |
| 2 | 37 | 0 | 1 |
| 3 | 92 | 0 | 0 |
| 4 | 76 | 0 | 0 |
| 5 | 39 | 0 | 3 |
| 6 | 59 | 0 | 8 |
| 7 | 87 | 0 | 4 |

It was observed that in different strains the compounds depresses or accelerates the fermentation process in tissue. The compound was observed to increase the ethanol production in some strains by as much as three times the natural rate, and depress the ethanol production in other strains by one-eighth its normal rate.

EXAMPLE 56

Inhibition of Pathogenic Strains of Androgen Receptor Containing Fungi

Pathogenic strains of Candida, Actinomyces, Norcardia, Cryptococci, Torulopsis, Aspergillus, Sporotrichum, Trichophyton, Blastomyces, Histoplasma, Microsporum and Coccidia have been analyzed for hormonal receptors. Estrogen, progesterone and androgen receptors were found in all strains of the above species.

The compound 2-(5-hydroxyhept-1-yl)bicyclo[3.3.0]octan-7-one {hexahydro-4-(5-hydroxyheptyl)-2(1H)-pentalenone} was tested for its receptor blocking ability in strains of the fungi. The anti-androgen was observed to block the androgen receptors form 29%–92% at concentrations of hormone:anti-androgen of 1:1 to 1:1,000.

| Genus | % Androgen Receptor Inhibition | % Estrogen Receptor Inhibition | % Progesterone Receptor Inhibition |
|---|---|---|---|
| Candida | 92 | 0 | 7 |
| Torulopsis | 77 | 0 | 6 |
| Actinomyces | 90 | 0 | 0 |
| Coccodia | 67 | 0 | 4 |
| Trichophyton | 81 | 0 | 7 |
| Blastomyces | 49 | 0 | 3 |
| Cryptococci | 76 | 0 | 4 |
| Sporotrichum | 29 | 0 | 7 |
| Norcardia | 50 | 0 | 0 |
| Histoplasma | 47 | 0 | 0 |

At the present time, therapies for fungal infections are not satisfactory and are frequently dangerous. The blocking ability of the novel compound of this invention holds much promise for medical application, in that efficacy studies and toxicity studies showed it to be efficacious and safe.

EXAMPLE 57

Management of Bacterial Organisms and Diseases

It has been observed clinically that certain infectious diseases are hormonally influenced, and this has been verified by several observations such as the premenopausal flare of pelvic inflammatory disease, the decreased incidence of pelvic inflammatory disease following menopause, the increase gingivitis following pregnancy as well as the increased severity of coccidious immitis that occurs during pregnancy (C. Drutz, "Lecture on Hormone and Microorganisms", Infectious Disease Society of America, Miami, Fla., Oct., 1982). An estrogen receptor has been identified in Brewers' yeast, Saccharomyces cervisiae (Feldman et al., Science, Vol. 218, page 297 (1982).

Because of these observations that hormones, even though they originated in the mammal, could influence bacteria and other microorganisms it was decided to evaluate the presence of hormonal receptors and their blockade by the anti-androgen of formula (I), and especially 2-(5-hydroxyhept-1-yl)bicyclo[3.3.0]octan-7-one {hexahydro-4-(5-hydroxyheptyl)-2(1H)-pentalenone}.

At least three strains each of *E. coli, Proteus, Pseudomonas, Serratieae, Bacteriodes, Staphylococci, Streptococci, Peptocci, Peptostreptococci, Fusiformis, Vierrella, Brucella, Pasteurella, Yersinia, Vibrio, Shigella, Salmonella* and *Clostridia* for bacterial organisms were tested with the compound 2-(5-hydroxyhept-1-yl)bicyclo[3.3.0]octan-7-one {hexahydro-4-(5-hydroxyheptyl)-2(1H)-pentalenone}. At least three strains of *Fusarium, Actinomyces, Norcardia, Cryptococci, Candium, Torulopsis, Coccidia, Aspergillus, Sporotrichum, Saccharomyces, Microsporum, Trichophyton, Histoplasma* and *Blastomyces* in the fungal families were tested with anti-androgen of this invention.

EXAMPLE 58

Bacterial Protocol

The microorganisms were grown overnight in an enriched trypticase soy broth. Three agar plates were enriched with 10% steroid-free heat inactivated free human serum. Anaerobic organisms were added also containing thioglycolinate. The cells were then incubated at seven different concentrations of labelled hormone between 0.1 and 10 nanomoles (nM). In order to avoid redundancy, *Pseudomonas testosteroni* is presented as a model in the following table:

| Pseudomonas Testosteroni Strain | % Androgen Receptor Inhibition | % Estrogen Receptor Inhibition | % Progesterone Receptor Inhibition |
|---|---|---|---|
| 1 | 90 | 0 | 0 |
| 2 | 49 | 0 | 0 |
| 3 | 39 | 0 | 0 |
| 4 | 63 | 0 | 0 |

It was observed that steroid receptors existed and that these receptors influenced bacterial growth. These data were consistent with those presented by previous investigators (Watanabe et al., *Journal of Steroid Chemistry*, Vol. 4, page 613 (1973).

The novel compound of the invention blocked between 39%–90% of these bacterial androgen receptors and concentrations of DHT:anti-androgen of 1:1,000.

EXAMPLE 59

The test procedures set forth in Examples 54–58 may be repeated with the compound 2-(5-methoxyhept-1-yl)bicyclo[3.3.0]octan-7-one {hexahydro-4-(5-methoxyheptyl)-2(1H)-pentalenone}. This compound has been determined to be an anti-androgenic compound operating in the same manner as the compound of the immediately preceding Example 58, and therefore may be used in its place in accordance with the method of the present invention.

EXAMPLE 60

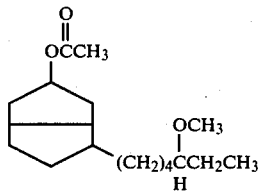

Alpha and beta isomers of
7-acetoxy-2-(5-methoxyhept-1-y)bicyclo [3.3.0]octane
{octahydro-4-(5-methoxyheptyl)-2-pentalenol acetate}

The procedure followed is the same as that described in Example 24 substituting 2-(5-methoxyhept-1-yl)bicyclo[3.3.0]-7octanol {octahydro-4-(5-methoxyheptyl)-2-pentalenol} (1.0 g, 4.0 mmoles), and glacial acetic acid (7 ml). The product is kugelrohred under reduced pressure leaving a clear, colorless oil (0.7 g, 2.5 mmoles).

Analysis: IR: 2931, 2856, 2820, 1736, 1462, 1394, 1374, 1358, 1328, 1315, 1305, 1245, 1155, 1095, 1050, 972, 916, 905, 744, and 719 cm$^{-1}$.

EXAMPLE 61

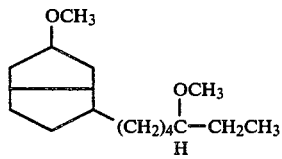

Alpha and beta isomers of
7-methoxy-2-(5-methoxyhept-1-y)bicyclo [3.3.0]octane
{octahydro-5-methoxy-1-(5-methoxyheptyl)pentalene}

The starting material, 2-(5-methoxyhept-1-yl)bicyclo[3.3.0]7 octanol {octahydro-4-(5-methoxyheptyl)-2-pentalenol} (1.0 g, 3.9 mmoles) is added to a reaction vessel containing sodium iodide (0.12 g, 4.9 mmoles) and tetrahydrofuran (12 ml). The solution is stirred while methyl iodide (0.84 g, 5.9 mmoles) is rapidly added. The reaction is heated in a 50° C. water bath for 4 hours. The water bath is removed and the reaction neutralized with the addition of water (5 ml). The organic phase is separated and the aqueous phase extracted with ether (2×50 ml). The ether extracts are combined and washed with brine (50 ml). The solution is dried over anhydrous magnesium sulfate and the solvent removed under vacuum leaving a clear yellow oil. The product is then kugelrohred under reduced pressure leaving a pale yellow oil (0.8 g, 3.1 mmoles).

Analysis: IR: 2932, 2856, 2816, 1461, 1362, 1240, 1189, 1152, 1121, 1095, and 979 cm$^{-1}$.

EXAMPLE 62

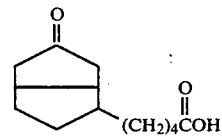

Alpha and beta isomers of
2-(4-carboxybutyl-1-yl)bicyclo[3.3.0]octan-7-one
{octahydro-5-oxo-1-pentalenepentanoic acid}

2-(5-Hydroxypent-1-yl)bicyclo[3.3.0]octan-7-one {hexahydro-4-(5-hydroxyheptyl)-2(1H)-pentalenone} (0.5 g, 2.4 mmoles) is mixed with a 10% solution of sodium carbonate (0.51 ml). The reaction is cooled in an ice bath and solution of potassium permanganate (0.48 g dissolved in 12 ml water) is slowly added over 10 minutes. The ice bath is then removed and the reaction mixture stirred at room temperature for 12 hour, after which time the precipitated manganese dioxide is filtered off and the filtrate partitioned between ether. The solution is acidified with dilute sulfuric acid and the organic layer separated. The aqueous phase is extracted with ether (2×20 ml), and the ether extracts combined and dried over anhydrous sodium sulfate. The solvent is removed under vacuum leaving a clear colorless oil. The crude product is chromatographed on silica gel and subsequently kugelrohred under reduced pressure leaving a clear, colorless oil (0.050 g, 0.22 mmoles).

Analysis: IR: 3300 (broad), 2928, 2856, 1728, 1459, 1402, 1259, 1245, 1235, 1195, 1177, 1069, 1049, 734, and 699 cm$^{-1}$.

EXAMPLE 63

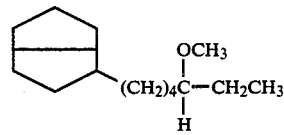

Alpha and Beta isomers of
2-(5-methoxyhept-1-yl)bicyclo[3.3.0]octane
{octahydro-1-(5-methoxyheptyl)pentalene}

2-(5-Methoxyhept-1-yl)bicyclo[3.3.0]octan-7-one {hexahydro-4-(5-methoxyheptyl)-2(1H)-pentalenone} (5 g, 19.8 mmoles) is mixed with diethylene glycol (27 ml) and potassium hydroxide (3.8 g, 6.7 mmoles). The reaction is stirred and mixed with 80% hydrazine hydrate (2.8 ml, 7.0 mmoles). The reaction is heated to 95° C. for 2 hours. After which time the temperature is increased to 200° C. and maintained with stirring for 5 hours. Then the reaction is cooled and added to 6N hydrochloric acid (200 ml). The solution is partitioned between ether and the phases separated. The aqueous phase is extracted with ether (2×100 ml) and the extracts combined. The ether solution is dried over anhydrous magnesium sulfate and the solvent removed under vacuum leaving a clear, purple oil. The crude product is kugelrohred under reduced pressure leaving a clear, colorless oil (4.0 g, 16.8 mmoles).

Analysis: IR: 2935, 2856, 2817, 1460, 1378, 1364, 1310, 1265, 1196, 1160, 1146, and 1096 cm$^{-1}$.

EXAMPLE 64

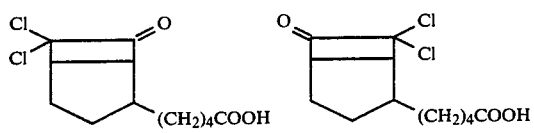

Alpha and Beta isomers of 6,6-dichloro-2-(4-carboxybut-1-yl)bicyclo[3.2.0]heptan-7-one {6,6-dichloro-7-oxobicyclo[3.2.0]heptane-2-pentanoic acid} and 7,7-dichloro-2-(4-carboxybut-1-yl) bicyclo [3.2.0]heptan-6-one {7,7-dichloro-6-oxobicyclo[3.2.0]heptane-2-pentanoic acid}

The procedure used is the same as that described in Example 62 with substituting 6,6-dichloro-2-(5-hydroxypent-1-yl) bicyclo[3.2.0]heptan-7-one {7,7-dichloro-4-(3-hydroxypentyl)bicyclo[3.2.0]heptan-6-one} and isomers (2.5 g, 9.5 mmoles), potassium permanganate (1.9 g, 2.2 mmoles) and sodium carbonate 10% (0.51 ml). The crude product is chromatographed on silica gel and kugelrohred under reduced pressure leaving a clear, colorless oil (1.2 g, 4.3 mmoles).

Analysis: IR: 2930, 2854, 1803, 1460, 1375, 1348, 1338, 1315, 1302, 1160, 1131, 1073, 1055, 1028, 990, 950, 810, and 745 cm$^{-1}$.

EXAMPLE 65

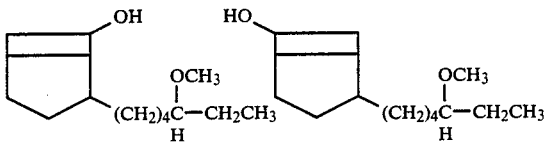

Alpha and Beta isomers of 2-(5-methoxyhept-1) bicyclo [3.2.0]heptan-7-ol {4-(5-methoxyheptyl)bicyclo [3.2.0]heptan-6-ol} and 5-(5-methoxtheptyl-1-yl)bicyclo [3.2.0]heptan-ol {2-(5-methoheptxyl)bicyclo [3.2.0]heptan-6-ol}

The procedure followed is the same as that described in Example 6 substituting 2-(5-methoxyhept-1-yl)bicyclo [3.2.0]heptan-7-one {4-(5-methoxyheptyl)bicyclo [3.2.0]heptan-6-one} and isomers (5 g, 0.020 moles), and sodium borohydride (1.5 g, 0.040 moles) in 95ethanol (50 ml). The crude oil produced is kugelrogred under reduced pressure leaving a clear, colorless oil (4.5 g, 0.019 moles).

Analysis: IR: 3400 (broad), 2960, 2935, 2855, 1461, 1385, 1365, 1334, 1235, 1195, 1150, 1093, and 925 cm$^{-1}$.

EXAMPLE 66

(4-Chloro-1-butyloxy)(2,2-dimethylethyl)dimethylsilane {(4-chlorobutoxy)(1,1-dimethylethyl)dimethylsilane}

The procedure followed is the same as that described in Example 7 substituting 4-chlorobutanol (326 g, 3.00 moles), tert-butyldimethylsilyl chloride (500 g, 3.31 moles), imidazole (225 g, 3.30 moles), and dimethylformamide (1600 ml). The crude product is fractionally distilled under reduced vacuum leaving a clear, colorless oil (475 g, 2.13 moles), BP a°C/0.3 mm.

Analysis: IR: 2982, 2928, 2889, 2855, 1469, 1462, 1443, 1387, 1359, 1277, 1255, 1106, 1005, 967, 835, 809, 774, 730, and 652 cm$^{-1}$.

EXAMPLE 67

3-(5-[1,1-Dimethylethyl)dimethylsiloxy]but-1-yl)cyclopentene {[4-(2-cyclopenten-1-yl)butoxy](1,1-dimethylethyl)-dimethylsilane}

The procedure followed is the same as that described in Example 8 with substituting (4-chloro-1-butyloxy)(2,2-dimethylethyl)dimethylsilane {(4-chlorobutoxy)(1,1-dimethylethyl)dimethylsilane} (476 g, 2.13 moles), tetrahydrofuran (500 ml), magnesium (96 g, 4.0 moles), 3-chlorocyclopentene (208 g, 2.0 moles), and Li$_2$CuCl$_4$ (6.4 mmoles). The resulting crude product is fractionally distilled under reduced pressure leaving a clear, colorless oil (100 g, 0.39 moles), BP 70° C/0.1 mm.

Analysis: IR: 3049, 2951, 2931, 2855, 1469, 1460, 1254, 1104, 1005, 834, 809, 773, 715, and 656 cm$^{-1}$.

EXAMPLE 68

3-(4-Hydroxybut-1-yl)cyclopentene {2-cyclopentene-1-butanol}

The procedure followed is the same as that described in Example 12 substituting 3-(5-[(1,1-dimethylethyl)-dimethylsiloxy]but-1-yl)cyclopentene {[4-(2-cyclopenten-1-yl)butoxy](1,1dimethylethyl)dimethylsilane} (100 g, 0.407 moles), 5% hydrofluoric acid (78 ml), acetonitrile (1500 ml). The crude product is kugelrohred under reduced pressure leaving a clear, colorless oil (51 g, 0.36 moles).

Analysis: IR: 3340 (broad), 3332, 3048, 2930, 2851, 1457, 1439, 1371, 1358, 1282, 1249, 1072, 1056, 1034, 983, 937, 910, and 715 cm$^{-1}$.

EXAMPLE 69

3-(4-Chlorobut-1-yl)cyclopentene {3-(4-chlorobutyl)cyclopentene}

3-(4-Hydroxybut-1-yl)cyclopentene {2-cyclopentene-1-butanol}(51 g, 0.37 moles) is diluted in dimethylformamide (100 ml) and added to pyridine (38 g, 0.40 moles). The solution is stirred and methane sulfonyl chloride (46 g, 0.40 moles) is added dropwise in the course of 10 minutes. The reaction is then heated in a 70° C. water bath for 30 minutes. Then the mixture is cooled and water (1 liter) is added over 20 minutes. The reaction is partitioned between hexane (500 ml) and the organic phase separated. The aqueous layer is extracted with hexane (2×500 ml) and the extracts combined with the organic layer. The solvent volume is reduced under vacuum and the residue dried over anhydrous magnesium sulfate. The solid is filtered off and the remaining solvent removed leaving a clear yellow oil. The crude product is fractionally distilled under reduced presure leaving a clear, colorless oil (43 g, 0.27 moles), BP 40° C./0.2 mm.

Analysis: IR: 3048, 2933, 2848, 1457, 1355, 1307, 1170, 910, 720, and 714 cm$^{-1}$.

EXAMPLE 70

3-(5-Hydroxyhept-1-yl)cyclopentene {alpha-ethyl-2-cyclopentene-1-pentanol}

All reactions are carried out under an inert atmosphere. 3-(4-Chlorobutyl-1) cyclopentene}3-(4-cholorobutyl)cyclopentene}(43 g, 0.27 moles) is diluted in tetrahydrofuran (50 ml) and added dropwise to a stirred, refluxing solution of tetrahydrofuran (200 ml) containing granular magnesium (30 g, 1.25 moles). After the addition is complete and the resulting Grignard salt has formed the reaction is refluxed an additional 2 hours. The reaction vessel is then cooled in a 0° C. ice bath and propionaldehyde (15.6 g, 0.27 moles) diluted in tetrahydrofuran (20 ml) is added dropwise over a period of 30 minutes. Then water (500 ml) is added over 30 minutes and the reaction warmed to room temperature. The reaction is partitioned between ether (500 ml) and the organic phase separated. The aqueous layer is extracted with ether (2×500 ml) and the ether extracts are combined. The product is washed with brine (500 ml) and the solvent volume reduced under vacuum. The residue is dried over anhydrous magnesium sulfate and the solid filtered out. The remaining solvent is removed leaving a clear yellow oil. The crude product is fractionally distilled under reduced pressure leaving the desired product as a clear, colorless oil (52 g, 0.29 moles), BP 76° C./0.25 mm.

Analysis: IR: 3387 (broad), 3048, 2925, 2849, 1459, 1440, 1374, 1368, 1357, 1117, 1062, 1034, 1028, 968, and 715 cm$^{-1}$.

Alternatively, to prepare longer chain homologues, other aldehydes can be substituted which include butyraldehyde, pentanal, etc., to form the corresponding derivatives e.g. 3-(5-hydroxyoct-1-yl)cyclopentene and 3-(5-hydroxyhept-1-yl)cyclopentene respectively. In addition the branched chain derivatives are easily formed by reacting the Grignard salt formed in Example 70 with acetone, 2-butanone, and other ketones to form 3-(5-methyl-5-hydroxyhex-1-yl)cyclopentene and 3-(5-methyl-5-hydroxy- hept-1-yl) cyclopentene, respectively. These intermediates can then be alkylated as described in Example 1 with, e.g., (methyl or ethyl iodide) and then reacted as described in Examples 16 and 17 to form the corresponding [3.2.0]and [3.3.0]bicyclo derivatives.

In addition the intermediate prepared in Example 70, 3-(5-hydroxypent-1-yl)cyclopentene {2-cyclopentene-1-pentanol} can be reacted by the same procedure described in Example 70 to form 3-(5-chloropent-1-yl)cyclopentene {3-(5-chloropentyl)cyclopentene} which can then be reacted as described in Example 17 to form the Grignard salt and thus can be used to form longer chain homologues in which the hydroxy group is on the 6 position. For example, reacting the Grignard salt with acetaldehyde forms 3-(6-hydroxyhept-1-yl)cyclopentene.

EXAMPLE 71

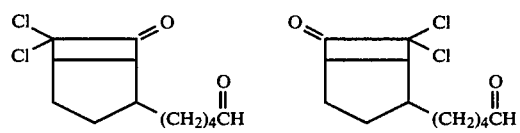

Alpha and Beta isomers of 6,6-dichloro-2-(4-formylbutyl)[3.2.0]heptan-7-one {6,6-dichloro-7-oxobicyclo[3.2.0]heptane-2-pentanol} and 7,7-dichloro-2-(4-formylbutyl)[3.2.0]heptan-6-one {7,7-dichloro-6-oxobicyclo [3.2.0]heptane-2-pentanol}

The procedure followed is the same as that described in Example 18 substituting 6,6-dichloro-2-(5-hydroxypent-1-yl)bicyclo[3.2.0]heptan-7-one {7,7-dichloro-4-(5-hydroxypentyl)bicyclo[3.2.0]heptan-6-one} and isomers (2.3 g, 8.6 mmoles), and pyridinium dichromate (6.4 g, 17.1 mmoles) dissolved in methylene chloride (18 ml). The crude product is chromatographed on silica gel and subsequently kugelrohred under reduced pressure leaving a clear, colorless oil (0.9 g, 3.4 mmoles).

Analysis: IR: 2931, 2855, 2715, 1803, 1726, 1460, 1370, 1330, 1318, 1305, 1276, 1223, 1160, 1073, 1055, 1027, 992, 957, 950, 915, 817, 735, and 673 cm$^{-1}$.

EXAMPLE 72

3-Chlorocyclohexene

2-Cyclohexenol (30 g, 0.31 moles), is dissolved in a solution of dimethylformamide (100 ml) and pyridine (38 g, 0.40 moles). The solution is stirred and methanesulfonyl chloride (46 g, 0.40 moles) is added dropwise over 20 minutes. The reaction is then heated in a 70° C. water bath for 30 minutes, after which time the mixture is cooled and water (1 liter) is added over 20 minutes. The mixture is partitioned between hexane (500 ml) and the organic phase separated. The aqueous layer is extracted with hexane (2×500 ml) and the extracts are combined. The solvent volume is reduced under vacuum and the residue dried over anhydrous magnesium sulfate. The solid is filtered off and the remaining solvent removed leaving a clear yellow oil. The crude product is kupelrohred under reduced pressure leaving a clear, colorless oil (37 g, 0.28 moles).

EXAMPLE 73

3-(5-Methoxyhept-1-yl)cyclohexene {3-(5-methoxyheptyl)cyclohexene}

All work is performed under an inert atmosphere. The Grignard salt of the intermediate prepared in Example 72 is prepared using activated magnesium. The reaction vessel is charged with potassium metal (9.7 g, 0.248 moles), anhydrous magnesium chloride (24 g, 0.252 moles), potassium iodide (41.8 g, 0.252) and tetrahydrofuran (350 ml). The mixture is stirred, heated under reflux for 3 hours, and then cooled to room temperature. The starting material, 3-chlorocyclohexene (30 g, 0.224 moles), diluted in tetrahydrofuran (50 ml), is added and the reaction heated under reflux for 12 hours. Then the mixture is cooled in a −20° C. ice water bath and Li$_2$CuCl$_4$ (0.6 mmoles) is added. The mixture is stirred for 10 minutes and 1-chloro-5-methoxyheptane (37 g, 0.224 moles), diluted in tetrahydrofuran, is added dropwise over 20 minutes. Then the mixture is poured into a saturated ammonium chloride solution and extracted with ether (500 ml) and water. The organic layer is separated and the aqueous layer extracted with ether (2×500 ml). The organic extracts are combined and the solvent is reduced under vacuum. The residue is washed with brine and then dried over anhydrous magnesium sulfate. The solid is filtered off and the remaining solvent removed leaving a clear, yellow oil. The crude product is chromatographed on silica gel and subsequently kugelrohred under reduced pressure leaving the product as a pale yellow oil (38 g, 0.13 moles).

Analysis: IR: 3055, 2925, 2900, 2865, 1469, 1378, 1355, 332, 1267, 1250, 1154, 1093, and 724 cm$^{-1}$.

EXAMPLE 74

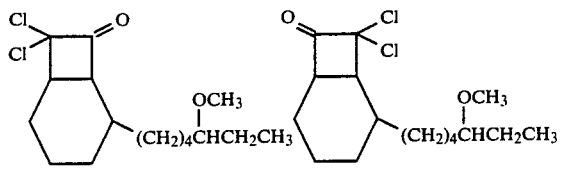

Alpha and Beta isomers of 7,7-dichloro-2-(5-methoxyhept-1-yl)bicyclo[4.2.0]octan-8-one {8,8-dichloro-5-(5-methoxyheptyl)bicyclo [4.2.0]octan-7-one} and 8,8-dichloro-2-(5-methoxyhept-1-yl)bicyclo[4.2.0]octan-7-one {8,8-dichloro-2-(5-methoxyheptyl)bicyclo [4.2.0]octan-7-one}

The procedure followed is the same as that described in Example 9 with the following substitutions made: the starting material prepared in Example 73, 3-(5-methoxyhept-1-yl) cyclohexene {3-(5-methoxyheptyl)cyclohexene} (38 g, 0.13 moles), trichloroacetyl chloride (43 g, 0.234 moles) and phosphorous oxychoride (39 g, 0.234 moles) both diluted in ether (100 ml), zinc/copper couple (17 g, 0.26 moles). The crude product is chromatographed on silica gel and subsequently kugelrohred under reduced pressure leaving the product as a clear, colorless oil (21 g, 0.065 moles).

Analysis: IR: 2925, 2900, 2865, 1803, 1469, 1378, 1355, 1332, 1267, 1250, 1154, 1093, and 724 cm$^{-1}$.

EXAMPLE 75

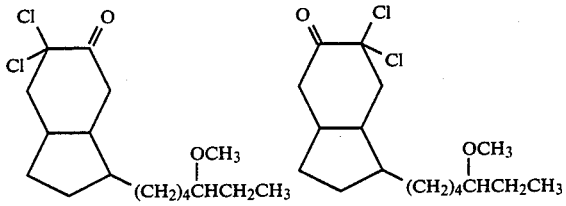

Alpha and Beta isomers of 7,7-dichloro-2-(5-methoxyhept-1-yl)bicyclo[4.3.0]nonan-8-one {6,6-dichlorooctahydro-3-(5-methoxy-heptyl)-5H-inden-5-one} and 8,8-dichloro-2-(5-methoxyhept-1-yl) bicyclo[4.3.0]nonan-7-one {6,6-dichlorooctahydro-3-(5-methoxyheptyl)-5H-inden-5-one}

The procedure followed is the same as that described in Example 28 with the following substitutions made: the starting material from Example 74, 7,7-dichloro-2-(5-methoxyhept-1-yl) bicyclo[4.2.0]octan-8-one {8,8-dichloro-5-(5-methoxyheptyl)bicyclo[4.2.0]octan-7-one} and isomers (21 g, 0.065 moles), ether diazomethane solution (282 ml), methanol (15 ml), and acetic acid (15 ml). After the acetic acid is added the solvent is removed under vacuum, leaving a clear yellow oil.

The crude product is then diluted with acetic acid (150 ml) and stirred while zinc powder (42 g) is slowly added. The reaction is heated in a 70° C. water bath for 1 hour, after which time ether (500 ml) is added and the solution is filtered. The filtrate is washed with brine (100 ml) and then with a solution of saturated bicarbonate. The ether layer is separated and dried over anhydrous sodium sulfate. The solvent is removed under vacuum leaving a clear yellow oil. This oily product can be dehalogenated by the method of Example 11 to yield alpha and beta isomers of 2-(5-methoxyhept-1-yl)bicyclo[4.3.0]nonan-8-one {octahydro-4-(5-methoxyheptyl)-2-(1H-indenone)}. The crude product is chromatographed on silica gel and subsequently kugelrohred under vacuum leaving a clear, colorless oil (5.1 g, 0.20 moles).

Analysis: IR: 2925, 2900, 2865, 1742, 1469, 1378, 1355, 332, 1267, 1250, 1154, 1093, 960, and 745 cm$^{-1}$.

EXAMPLE 76

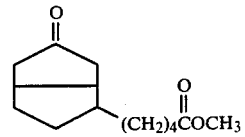

Alpha and beta isomers of 2-(4-carboxybut-1-yl)bicyclo[3.3.0]octan-7-one methyl ester {methyl octahydro-5-oxo-1-pentalene-pentanoate}

The starting material prepared in Example 62, 2-(5-carboxybut-1-yl)bicyclo[3.3.0]octan-7-one {octahydro-5-oxo-1-pentalenepentanoic acid} (1 g, 4.4 mmoles) is diluted in absolute methanol (20 ml). The solution is stirred and concentrated sulfuric acid (0.5 g) is added. The solution is stirred under reflux for 4 hours, after which time the reaction mixture is partitioned between the organic phase (25 ml) and aqueous phase (50 ml). The organic phase is separated and the aqeuous phase extracted with ether (2×20 ml). The ether extracts are combined and dried over anhydrous magnesium sulfate. The solid is filtered off and the solvent removed under vacuum leaving a yellow oil. The product is chromatographed on silica gel and kugelrohred under reduced pressure leaving the product as a clear, colorless oil (0.4 g, 1.7 mmoles).

Analysis: IR: 2934, 2856, 1739, 1725, 1462, 1404, 1385, 1365, 1239, 1165, and 1044 cm$^{-1}$.

What is claimed is:

1. A method of blocking androgen receptor sites in a mammal which comprises applying to said sites an effective anti-androgenic dose of a compound of the formula

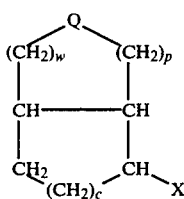

wherein

Q is CO, CH(OR), or CR(OH), R being H or $C^{1-2}$-alkyl;

X is hydroxy-$C^{2-9}$-alkyl, methoxy-$C^{2-9}$-alkyl, ethoxy-$C_{2-9}$-alkyl, oxo-$C^{2-9}$-alkyl, formyl-$C^{2-9}$-alkyl, carboxy-$C^{2-9}$-alkyl, or ($C^{1-2}$-alkyl) oxycarbonyl-$C^{2-9}$-alkyl, c is 1 or 2;

p and w are 0, 1, or 2 and the sum of p and w is 1 to 4; or a pharmaceutically aceptable salt thereof.

2. A method of claim 1, wherein the compound has the formula

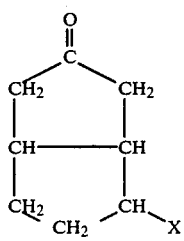

X being —(CH$_2$)$_4$CH(OH)CH$_2$CH$_3$, —(CH$_2$)$_4$CH(OCH$_3$)CH$_2$CH$_3$, —(CH$_2$)$_4$CH(OCOCH$_3$)C$_2$H$_5$, —(CH$_2$)$_5$OCO—CH$_3$, —(CH$_2$)$_4$COOCH$_3$, —(CH$_2$)$_4$CH(OCH$_2$CH$_3$)CH$_2$CH$_3$, —(CH$_2$)$_4$COCH$_2$CH$_3$, or —(CH$_2$)$_4$CH$_2$OH.

3. A method of claim 1 wherein the compound is 2-(5-methoxyhept-1-yl) bicyclo [3.3.0]octan-7-one.

4. A method of claim 1 wherein the compound is 2-(5-hydroxylhept-1-yl) bicyclo [3.3.0]octan-7-one.

5. A method of claim 1 wherein the compound is 2-(5-ethyoxyhept-1-yl) bicyclo [3.3.0]octan-7-one.

6. A method of claim 1, wherein said compound is topically applied.

7. A method of claim 6, wherein said mammal is a patient afflicted with acne.

8. A method of claim 6 for suppressing the formation of keloids which comprises topically applying to said mammal an effective anti-androgenic compound of claim to the skin of said mammal whereby androgen receptor sites are blocked, thereby retarding the formation of keloids.

9. A method of controlling a microorganism which has androgen receptor sites whereby androgen is taken into the system of the microorganism, which method comprises blocking said androgen receptor sites by administering to said microorganism an effective anti-androgenic dose of a compound of the formula:

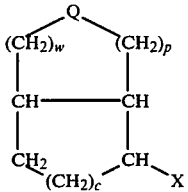

wherein

Q is CO, CH(OR), or CR(OH), R being H or $C^{1-2}$-alkyl;

X is hydroxy-$C^{2-9}$-alkyl, methoxy-$C^{2-9}$-alkyl, ethyoxy$C^{2-9}$-alkyl, oxo-$C^{2-9}$-alkyl, formyl-$C^{2-9}$-alkyl, carboxy-$C^{2-9}$-alkyl, or ($C^{1-2}$-alkyl) oxycarbonyl-$C^{2-9}$-alkyl, c, is 1 or 2;

p and w are 0,1, or 2 and the sum of p and w is 1 to 4; or a pharmaceutically acceptable salt thereof by contacting said anti-androgenic agent with said microorganism, whereby androgen receptor sites are blocked, thereby blocking the uptake of androgen by said microorganism.

10. A method of claim 9, wherein the compound has the formula

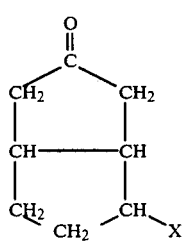

X being —(CH$_2$)$_4$CH(OH)CH$_2$CH$_3$, —(CH$_2$)$_4$CH(OCH$_3$)CH$_2$CH$_3$, —(CH$_2$)$_4$CH(OCOCH$_3$)C$_2$H$_3$, —(CH$_2$)$_5$0OCO—CH$_3$, —(CH$_2$)$_4$COOCH$_3$, —(CH$_2$)$_4$CH(OCH$_2$CH$_3$)CH$_2$CH$_3$, —(CH$_2$)$_4$COCH$_2$CH$_3$, or —(CH$_2$)$_4$CH$_2$OH.

11. A method of claim 9 wherein the compound is 2-(5-methoxyhept-1-yl)bicyclo [3.3.0]octane 7-one.

12. A method of claim 9 wherein the compound is 2-(5-hydroxypept-1-yl)bicyclo [3.3.0]octan-7-one.

13. A method of claim 9 wherein the compound is 2-(5-ethyoxyhept1-yl)bicyclo [3.3.0]octan-7-one.

14. A method of claim 9 wherein said microorganism is a fungus.

15. A method of claim 9 wherein said microorganism is a bacterium.

16. A method of claim 9 wherein said anti-androgenic agent is contained in an aqueous solution.

17. A method of claim 16 wherein said aqueous solution contains from about 0.001 to about 0.5 parts by weight of said anti-androgenic agent.

18. A method of claim 14 wherein said fungus is a Fusarium.

19. A method of claim 9 for controlling the rate of a fungal fermentation process wherein the fungus undergoing fermentation is one which has androgen receptor sites whereby androgen is taken into the system of the fungus which comprises blocking said androgen receptor sites by adding to the fermentation mixture an effective anti-androgenic amount of a compound of claim 1 to said fungus, whereby androgen receptor sites are blocked, thereby blocking the uptake of androgen by said microorganism.

* * * * *

UNITED STATES PATENT AND TRADEMARK OFFICE
CERTIFICATE OF CORRECTION

PATENT NO. : 4,689,345

DATED : August 25, 1987

INVENTOR(S) : Walter J. KASHA et al.

It is certified that error appears in the above-identified patent and that said Letters Patent is hereby corrected as shown below:

Title page, item [63], "Related U.S. Application Data," line 6, change "560,310" to --546,310--.

Signed and Sealed this

Eighth Day of December, 1992

Attest:

DOUGLAS B. COMER

*Attesting Officer*       *Acting Commissioner of Patents and Trademarks*